(12) United States Patent
Patrick et al.

(10) Patent No.: US 10,758,374 B2
(45) Date of Patent: Sep. 1, 2020

(54) CARPOMETACARPAL (CMC) IMPLANTS AND METHODS

(71) Applicant: Cartiva, Inc., Alpharetta, GA (US)

(72) Inventors: Timothy J. Patrick, Roswell, GA (US); Carribeth B. Ramey, Suwanee, GA (US); Letitia Tudor, Suwanee, GA (US)

(73) Assignee: CARTIVA, INC., Alpharetta, GA (US)

( * ) Notice: Subject to any disclaimer, the term of this patent is extended or adjusted under 35 U.S.C. 154(b) by 126 days.

(21) Appl. No.: 15/085,796

(22) Filed: Mar. 30, 2016

(65) Prior Publication Data
US 2016/0287407 A1 Oct. 6, 2016

Related U.S. Application Data

(60) Provisional application No. 62/141,186, filed on Mar. 31, 2015.

(51) Int. Cl.
*A61F 2/30* (2006.01)
*A61B 17/17* (2006.01)
(Continued)

(52) U.S. Cl.
CPC ........ *A61F 2/4606* (2013.01); *A61B 17/1686* (2013.01); *A61F 2/4241* (2013.01);
(Continued)

(58) Field of Classification Search
CPC ............ A61F 2/4241; A61F 2002/4258; A61F 2/4261; A61F 2002/30301; A61F 2002/30754; A61F 2/30756; A61F 2002/4276; A61F 2002/4256; A61F 2/42; A61F 2230/0004; A61F 2/4606; A61F 2002/302; A61F 2002/4627; A61F 2230/0065
See application file for complete search history.

(56) References Cited

U.S. PATENT DOCUMENTS

| | | |
|---|---|---|
| 3,276,996 A | 10/1966 | Lazare |
| 3,663,470 A | 5/1972 | Nishimura et al. |
| | (Continued) | |

FOREIGN PATENT DOCUMENTS

| | | |
|---|---|---|
| DE | 20218703 U1 | 3/2003 |
| EP | 0222404 A1 | 5/1987 |
| | (Continued) | |

OTHER PUBLICATIONS

Andrade et al., "Water as a Biomaterial," Trans. Am. Soc. Artif. Intern. Organs, 19:1 (1973).
(Continued)

*Primary Examiner* — Ann Schillinger
(74) *Attorney, Agent, or Firm* — Duane Morris LLP

(57) ABSTRACT

Implants suitable for use in a carpometacarpal joint includes an upper surface, a lower surface, and sidewalls extending between the upper surface and the lower surface. The implant includes hydrogel material such as polyvinyl alcohol (PVA) hydrogel. Kits can include systems for preparing an implantation site, creating a cavity, and/or deploying the implant. Methods of treating a carpometacarpal joint include deploying an implant in a recess in a carpometacarpal bone.

23 Claims, 31 Drawing Sheets

(51) Int. Cl.
  *A61F 2/46* (2006.01)
  *A61B 17/16* (2006.01)
  *A61F 2/42* (2006.01)
(52) U.S. Cl.
  CPC .......... *A61F 2/4657* (2013.01); *A61F 2/3094* (2013.01); *A61F 2/30942* (2013.01); *A61F 2002/30075* (2013.01); *A61F 2002/30224* (2013.01); *A61F 2002/30301* (2013.01); *A61F 2002/30677* (2013.01); *A61F 2002/4258* (2013.01); *A61F 2002/4627* (2013.01); *A61F 2002/4662* (2013.01)

(56) References Cited

U.S. PATENT DOCUMENTS

| | | |
|---|---|---|
| 3,673,612 A | 7/1972 | Merrill et al. |
| 3,849,238 A | 11/1974 | Gould et al. |
| 3,859,421 A | 1/1975 | Hucke |
| 4,083,906 A | 4/1978 | Schindler et al. |
| 4,158,684 A | 6/1979 | Klawitter et al. |
| 4,205,400 A | 6/1980 | Shen et al. |
| 4,351,069 A | 9/1982 | Ballintyn et al. |
| 4,472,542 A | 9/1984 | Nambu |
| 4,517,295 A | 5/1985 | Bracke et al. |
| 4,524,064 A | 6/1985 | Nambu |
| 4,609,337 A | 9/1986 | Wichterle et al. |
| 4,663,358 A | 5/1987 | Hyon et al. |
| 4,664,857 A | 5/1987 | Nambu |
| 4,693,939 A | 9/1987 | Ofstead |
| 4,731,081 A | 3/1988 | Tiffany et al. |
| 4,734,097 A | 3/1988 | Tanabe et al. |
| 4,738,255 A | 4/1988 | Goble et al. |
| 4,753,761 A | 6/1988 | Suzuki |
| 4,759,766 A | 7/1988 | Buttner-Janz et al. |
| 4,772,284 A | 9/1988 | Suzuki |
| 4,784,990 A | 11/1988 | Nimrod et al. |
| 4,787,905 A | 11/1988 | Loi |
| 4,808,353 A | 2/1989 | Nambu et al. |
| 4,828,493 A | 5/1989 | Nambu et al. |
| 4,851,168 A | 7/1989 | Graiver et al. |
| 4,911,720 A | 3/1990 | Collier |
| 4,916,170 A | 4/1990 | Nambu |
| 4,946,461 A | 8/1990 | Fischer |
| 4,988,761 A | 1/1991 | Ikada et al. |
| 4,995,882 A | 2/1991 | Destouet et al. |
| 5,047,055 A | 9/1991 | Bao et al. |
| 5,080,674 A | 1/1992 | Jacobs et al. |
| 5,095,037 A | 3/1992 | Iwamitsu et al. |
| 5,106,743 A | 4/1992 | Franzblau et al. |
| 5,106,876 A | 4/1992 | Kawamura |
| 5,108,428 A | 4/1992 | Capecchi et al. |
| 5,108,436 A | 4/1992 | Chu et al. |
| 5,118,667 A | 6/1992 | Adams et al. |
| 5,141,973 A | 8/1992 | Kobayashi et al. |
| 5,171,322 A | 12/1992 | Kenny |
| 5,171,574 A | 12/1992 | Kuberasampath et al. |
| 5,192,326 A | 3/1993 | Bao et al. |
| 5,206,023 A | 4/1993 | Hunziker |
| 5,219,360 A | 6/1993 | Georgiade |
| 5,234,456 A | 8/1993 | Silvestrini |
| 5,244,799 A | 9/1993 | Anderson |
| 5,258,023 A | 11/1993 | Reger |
| 5,258,042 A | 11/1993 | Mehta |
| 5,258,043 A | 11/1993 | Stone |
| 5,260,066 A | 11/1993 | Wood et al. |
| 5,287,857 A | 2/1994 | Mann |
| 5,288,503 A | 2/1994 | Wood et al. |
| 5,290,494 A | 3/1994 | Coombes et al. |
| 5,314,477 A | 5/1994 | Marnay |
| 5,314,478 A | 5/1994 | Oka et al. |
| 5,326,364 A | 7/1994 | Clift, Jr. et al. |
| 5,336,551 A | 8/1994 | Gravier et al. |
| 5,336,767 A | 8/1994 | Della Valle et al. |
| 5,343,877 A | 9/1994 | Park |
| 5,344,459 A | 9/1994 | Swartz |
| 5,346,935 A | 9/1994 | Suzuki et al. |
| 5,397,572 A | 3/1995 | Coombes et al. |
| 5,399,591 A | 3/1995 | Smith et al. |
| 5,401,269 A | 3/1995 | Buttner-Janz et al. |
| 5,409,904 A | 4/1995 | Hecht et al. |
| 5,410,016 A | 4/1995 | Hubbell et al. |
| 5,442,053 A | 8/1995 | Della Valle et al. |
| 5,458,643 A | 10/1995 | Oka et al. |
| 5,458,645 A | 10/1995 | Bertin |
| 5,486,197 A | 1/1996 | Le et al. |
| 5,489,310 A | 2/1996 | Mikhail |
| 5,490,962 A | 2/1996 | Cima et al. |
| 5,492,697 A | 2/1996 | Boyan et al. |
| 5,494,940 A | 2/1996 | Unger et al. |
| 5,502,082 A | 3/1996 | Unger et al. |
| 5,512,475 A | 4/1996 | Naughton et al. |
| 5,522,898 A | 6/1996 | Bao |
| 5,534,028 A | 7/1996 | Bao et al. |
| 5,541,234 A | 7/1996 | Unger et al. |
| 5,545,229 A | 8/1996 | Parsons et al. |
| 5,549,690 A | 8/1996 | Hollister et al. |
| 5,556,429 A | 9/1996 | Felt |
| 5,556,431 A | 9/1996 | Buttner-Janz |
| 5,578,217 A | 11/1996 | Unger et al. |
| 5,601,562 A | 2/1997 | Wolf et al. |
| 5,626,861 A | 5/1997 | Laurencin et al. |
| 5,645,592 A | 7/1997 | Nicolais et al. |
| 5,645,605 A | 7/1997 | Klawitter |
| 5,656,450 A | 8/1997 | Boyan et al. |
| 5,658,329 A | 8/1997 | Purkait |
| 5,674,241 A | 10/1997 | Bley et al. |
| 5,674,295 A | 10/1997 | Ray et al. |
| 5,674,296 A | 10/1997 | Bryan et al. |
| 5,688,459 A | 11/1997 | Mao et al. |
| 5,700,289 A | 12/1997 | Breitbart et al. |
| 5,705,780 A | 1/1998 | Bao |
| 5,716,416 A | 2/1998 | Lin |
| 5,750,585 A | 5/1998 | Park et al. |
| 5,766,618 A | 6/1998 | Laurencin et al. |
| 5,769,897 A | 6/1998 | Harle |
| 5,769,899 A | 6/1998 | Schwartz et al. |
| 5,789,464 A | 8/1998 | Muller |
| 5,795,353 A | 8/1998 | Felt |
| 5,824,093 A | 10/1998 | Ray et al. |
| 5,824,094 A | 10/1998 | Serhan et al. |
| 5,844,016 A | 12/1998 | Sawhney et al. |
| 5,847,046 A | 12/1998 | Jiang et al. |
| 5,855,610 A | 1/1999 | Vacanti et al. |
| 5,863,297 A | 1/1999 | Walter et al. |
| 5,863,551 A | 1/1999 | Woerly |
| 5,876,452 A | 3/1999 | Anthanasiou et al. |
| 5,876,741 A | 3/1999 | Ron |
| 5,880,216 A | 3/1999 | Tanihara et al. |
| 5,882,351 A | 3/1999 | Fox |
| 5,900,245 A | 5/1999 | Sawhney et al. |
| 5,916,585 A | 6/1999 | Cook et al. |
| 5,925,626 A | 7/1999 | Della Valle et al. |
| 5,928,239 A | 7/1999 | Mirza |
| 5,935,129 A | 8/1999 | McDevitt et al. |
| 5,944,754 A | 8/1999 | Vacanti |
| 5,947,844 A | 9/1999 | Shimosaka et al. |
| 5,948,829 A | 9/1999 | Wallajapet et al. |
| 5,957,787 A | 9/1999 | Hwang |
| 5,976,186 A | 11/1999 | Bao et al. |
| 5,981,826 A | 11/1999 | Ku et al. |
| 6,001,352 A | 12/1999 | Boyan et al. |
| 6,027,744 A | 2/2000 | Vacanti et al. |
| 6,060,534 A | 5/2000 | Ronan et al. |
| 6,093,205 A | 7/2000 | McLeod et al. |
| 6,102,954 A | 8/2000 | Albrektsson et al. |
| 6,103,255 A | 8/2000 | Levene et al. |
| 6,132,465 A | 10/2000 | Ray et al. |
| 6,156,067 A | 12/2000 | Bryan et al. |
| 6,171,610 B1 | 1/2001 | Vacanti et al. |
| 6,187,329 B1 | 2/2001 | Agrawal et al. |
| 6,206,927 B1 | 3/2001 | Fell |
| 6,224,630 B1 | 5/2001 | Bao et al. |
| 6,231,605 B1 | 5/2001 | Ku |

(56) References Cited

U.S. PATENT DOCUMENTS

| | | |
|---|---|---|
| 6,245,026 B1 | 6/2001 | Campbell |
| 6,255,359 B1 | 7/2001 | Agrawal et al. |
| 6,264,695 B1 | 7/2001 | Stoy |
| 6,268,405 B1 | 7/2001 | Yao et al. |
| 6,271,278 B1 | 8/2001 | Park et al. |
| 6,280,475 B1 | 8/2001 | Bao et al. |
| 6,334,044 B1 | 12/2001 | Wasai et al. |
| 6,337,198 B1 | 1/2002 | Levene et al. |
| 6,340,369 B1 | 1/2002 | Ferree |
| 6,341,952 B2 | 1/2002 | Gaylo et al. |
| 6,344,058 B1 | 2/2002 | Ferree |
| 6,355,699 B1 | 3/2002 | Vyakarnam et al. |
| 6,358,251 B1 | 3/2002 | Mirza |
| 6,371,984 B1 | 4/2002 | Van Dyke et al. |
| 6,376,573 B1 | 4/2002 | White et al. |
| 6,379,962 B1 | 4/2002 | Holy et al. |
| 6,383,519 B1 | 5/2002 | Sapieszko et al. |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,576 B1 | 8/2002 | Haldimann |
| 6,451,059 B1 | 9/2002 | Janas et al. |
| 6,472,210 B1 | 10/2002 | Holy et al. |
| 6,482,234 B1 | 11/2002 | Weber et al. |
| 6,531,523 B1 | 3/2003 | Davankov et al. |
| 6,533,818 B1 | 3/2003 | Weber et al. |
| 6,534,084 B1 | 3/2003 | Vyakarnam et al. |
| 6,558,421 B1 | 5/2003 | Fell et al. |
| 6,602,291 B1 | 8/2003 | Ray et al. |
| 6,607,558 B2 | 8/2003 | Kuras |
| 6,610,094 B2 | 8/2003 | Husson |
| 6,629,997 B2 | 10/2003 | Mansmann |
| 6,645,248 B2 | 11/2003 | Casutt |
| 6,667,049 B2 | 12/2003 | Janas et al. |
| 6,679,917 B2 | 1/2004 | Ek |
| 6,686,437 B2 | 2/2004 | Buchman et al. |
| 6,707,558 B2 | 3/2004 | Bennett |
| 6,710,126 B1 | 3/2004 | Hirt et al. |
| 6,726,721 B2 | 4/2004 | Stoy et al. |
| 6,733,533 B1 | 5/2004 | Lozier |
| 6,734,000 B2 | 5/2004 | Chin et al. |
| 6,740,118 B2 | 5/2004 | Eisermann et al. |
| 6,773,713 B2 | 8/2004 | Bonassar et al. |
| 6,783,546 B2 | 8/2004 | Zucherman et al. |
| 6,783,721 B2 | 8/2004 | Higham et al. |
| 6,800,298 B1 | 10/2004 | Burdick et al. |
| 6,802,863 B2 | 10/2004 | Lawson et al. |
| 6,827,743 B2 | 12/2004 | Eisermann et al. |
| 6,840,960 B2 | 1/2005 | Bubb |
| 6,849,092 B2 | 2/2005 | Van Dyke et al. |
| 6,855,743 B1 | 2/2005 | Gvozdic |
| 6,875,232 B2 | 4/2005 | Nigam |
| 6,875,386 B1 | 4/2005 | Ward et al. |
| 6,875,442 B2 | 4/2005 | Holy et al. |
| 6,878,384 B2 | 4/2005 | Cruise et al. |
| 6,881,228 B2 | 4/2005 | Zdeblick et al. |
| 6,893,463 B2 | 5/2005 | Fell |
| 6,893,466 B2 | 5/2005 | Trieu |
| 6,923,811 B1 | 8/2005 | Carl et al. |
| 6,960,617 B2 | 11/2005 | Omidian et al. |
| 6,982,298 B2 | 1/2006 | Calabro et al. |
| 6,993,406 B1 | 1/2006 | Cesarano, III et al. |
| 7,008,635 B1 | 3/2006 | Coury et al. |
| 7,012,034 B2 | 3/2006 | Heide et al. |
| 7,022,522 B2 | 4/2006 | Guan et al. |
| 7,029,479 B2 | 4/2006 | Tallarida et al. |
| 7,048,766 B2 | 5/2006 | Ferree |
| 7,052,515 B2 | 5/2006 | Simonson |
| 7,060,097 B2 | 6/2006 | Fraser et al. |
| 7,066,958 B2 | 6/2006 | Ferree |
| 7,066,960 B1 | 6/2006 | Dickman |
| 7,083,649 B2 | 8/2006 | Zucherman et al. |
| 7,091,191 B2 | 8/2006 | Laredo et al. |
| 7,156,877 B2 | 1/2007 | Lotz et al. |
| 7,186,419 B2 | 3/2007 | Petersen |
| 7,201,774 B2 | 4/2007 | Ferree |
| 7,201,776 B2 | 4/2007 | Ferree et al. |
| 7,214,245 B1 | 5/2007 | Marcolongo et al. |
| 7,217,294 B2 | 5/2007 | Kusanagi et al. |
| 7,235,592 B2 | 6/2007 | Muratoglu et al. |
| 7,250,060 B2 | 7/2007 | Trieu |
| 7,258,692 B2 | 8/2007 | Thelen et al. |
| 7,264,634 B2 | 9/2007 | Schmieding |
| 7,282,165 B2 | 10/2007 | Williams, III et al. |
| 7,291,169 B2 | 11/2007 | Hodorek |
| 7,316,919 B2 | 1/2008 | Childs et al. |
| 7,332,117 B2 | 2/2008 | Higham et al. |
| 7,357,798 B2 | 4/2008 | Sharps et al. |
| 7,377,942 B2 | 5/2008 | Berry |
| 7,682,540 B2 | 3/2010 | Boyan et al. |
| 7,731,988 B2 | 6/2010 | Thomas et al. |
| 7,745,532 B2 | 6/2010 | Ruberti et al. |
| 7,828,853 B2 | 11/2010 | Ek et al. |
| 7,910,124 B2 | 3/2011 | Boyan et al. |
| 7,985,781 B2 | 7/2011 | Muratoglu et al. |
| 8,002,830 B2 | 8/2011 | Boyan et al. |
| 8,142,808 B2 | 3/2012 | Boyan et al. |
| 8,318,192 B2 | 11/2012 | Boyan et al. |
| 8,334,044 B2 | 12/2012 | Myung et al. |
| 8,475,503 B2 | 7/2013 | Denoziere et al. |
| 8,486,436 B2 | 7/2013 | Boyan et al. |
| 8,709,045 B1 | 4/2014 | Folsom |
| 8,895,073 B2 | 11/2014 | Boyan et al. |
| 9,155,543 B2 | 10/2015 | Walsh et al. |
| 9,526,632 B2 | 12/2016 | Walsh et al. |
| 9,545,310 B2 | 1/2017 | Maher et al. |
| 9,737,294 B2 | 8/2017 | Wales et al. |
| 9,907,663 B2 | 3/2018 | Patrick et al. |
| 2001/0016741 A1* | 8/2001 | Burkus ............... A61B 17/025 606/57 |
| 2001/0029399 A1 | 10/2001 | Ku |
| 2001/0038831 A1 | 11/2001 | Park et al. |
| 2001/0039455 A1 | 11/2001 | Simon et al. |
| 2001/0046488 A1 | 11/2001 | Vandenburgh et al. |
| 2002/0026244 A1 | 2/2002 | Trieu |
| 2002/0031500 A1 | 3/2002 | MacLaughlin et al. |
| 2002/0034646 A1 | 3/2002 | Canham |
| 2002/0072116 A1 | 6/2002 | Bhatia et al. |
| 2002/0140137 A1 | 10/2002 | Sapieszko et al. |
| 2002/0173855 A1 | 11/2002 | Mansmann |
| 2002/0183845 A1 | 12/2002 | Mansmann |
| 2002/0183848 A1 | 12/2002 | Ray et al. |
| 2002/0187182 A1 | 12/2002 | Kramer et al. |
| 2003/0008395 A1 | 1/2003 | Holy et al. |
| 2003/0008396 A1 | 1/2003 | Ku |
| 2003/0021823 A1 | 1/2003 | Landers et al. |
| 2003/0055505 A1 | 3/2003 | Sicotte et al. |
| 2003/0059463 A1 | 3/2003 | Lahtinen |
| 2003/0082808 A1 | 5/2003 | Guan et al. |
| 2003/0175656 A1 | 9/2003 | Livne et al. |
| 2003/0176922 A1 | 9/2003 | Lawson et al. |
| 2003/0199984 A1 | 10/2003 | Trieu |
| 2003/0220695 A1 | 11/2003 | Sevrain |
| 2003/0233150 A1 | 12/2003 | Bourne et al. |
| 2003/0236573 A1 | 12/2003 | Evans et al. |
| 2004/0010048 A1 | 1/2004 | Evans et al. |
| 2004/0024465 A1 | 2/2004 | Lambrecht et al. |
| 2004/0034434 A1* | 2/2004 | Evans ............... A61L 27/12 623/23.51 |
| 2004/0044412 A1 | 3/2004 | Lambrecht et al. |
| 2004/0052867 A1 | 3/2004 | Canham |
| 2004/0059415 A1 | 3/2004 | Schmieding |
| 2004/0059425 A1 | 3/2004 | Schmieding |
| 2004/0063200 A1 | 4/2004 | Chaikof et al. |
| 2004/0064195 A1 | 4/2004 | Herr |
| 2004/0073312 A1 | 4/2004 | Eisermann et al. |
| 2004/0092653 A1 | 5/2004 | Ruberti et al. |
| 2004/0117022 A1 | 6/2004 | Marnay et al. |
| 2004/0143327 A1 | 7/2004 | Ku |
| 2004/0143329 A1 | 7/2004 | Ku |
| 2004/0143333 A1 | 7/2004 | Bain et al. |
| 2004/0147016 A1 | 7/2004 | Rowley et al. |
| 2004/0171143 A1 | 9/2004 | Chin et al. |
| 2004/0172135 A1 | 9/2004 | Mitchell |

(56) References Cited

U.S. PATENT DOCUMENTS

| | | |
|---|---|---|
| 2004/0220296 A1 | 11/2004 | Lowman et al. |
| 2004/0220669 A1 | 11/2004 | Studer |
| 2004/0220670 A1 | 11/2004 | Eisermann et al. |
| 2004/0249465 A1 | 12/2004 | Ferree |
| 2005/0037052 A1 | 2/2005 | Udipi et al. |
| 2005/0043733 A1 | 2/2005 | Eisermann et al. |
| 2005/0043802 A1 | 2/2005 | Eisermann et al. |
| 2005/0049706 A1 | 3/2005 | Brodke et al. |
| 2005/0055094 A1 | 3/2005 | Kuslich |
| 2005/0055099 A1 | 3/2005 | Ku |
| 2005/0071003 A1 | 3/2005 | Ku |
| 2005/0074877 A1 | 4/2005 | Mao |
| 2005/0079200 A1 | 4/2005 | Rathenow et al. |
| 2005/0090901 A1 | 4/2005 | Studer |
| 2005/0096744 A1 | 5/2005 | Trieu et al. |
| 2005/0106255 A1 | 5/2005 | Ku |
| 2005/0137677 A1 | 6/2005 | Rush |
| 2005/0137707 A1 | 6/2005 | Malek |
| 2005/0143826 A1 | 6/2005 | Zucherman et al. |
| 2005/0149196 A1 | 7/2005 | Zucherman et al. |
| 2005/0154462 A1 | 7/2005 | Zucherman et al. |
| 2005/0154463 A1 | 7/2005 | Trieu |
| 2005/0169963 A1 | 8/2005 | Van Dyke et al. |
| 2005/0171608 A1 | 8/2005 | Peterman et al. |
| 2005/0177238 A1 | 8/2005 | Khandkar et al. |
| 2005/0209704 A1 | 9/2005 | Maspero et al. |
| 2005/0216087 A1 | 9/2005 | Zucherman et al. |
| 2005/0228500 A1 | 10/2005 | Kim et al. |
| 2005/0233454 A1 | 10/2005 | Nies et al. |
| 2005/0244449 A1 | 11/2005 | Sayer et al. |
| 2005/0260178 A1 | 11/2005 | Vandenburgh et al. |
| 2005/0261682 A1 | 11/2005 | Ferree |
| 2005/0273176 A1 | 12/2005 | Ely et al. |
| 2005/0277921 A1 | 12/2005 | Eisermann et al. |
| 2005/0278025 A1 | 12/2005 | Ku et al. |
| 2005/0287187 A1 | 12/2005 | Mansmann |
| 2006/0002890 A1 | 1/2006 | Hersel et al. |
| 2006/0052874 A1 | 3/2006 | Johnson et al. |
| 2006/0052875 A1 | 3/2006 | Bernero et al. |
| 2006/0052878 A1 | 3/2006 | Schmieding |
| 2006/0058413 A1 | 3/2006 | Leistner et al. |
| 2006/0064172 A1 | 3/2006 | Trieu |
| 2006/0064173 A1 | 3/2006 | Guederian |
| 2006/0083728 A1 | 4/2006 | Kusanagi et al. |
| 2006/0100304 A1 | 5/2006 | Vresilovic et al. |
| 2006/0121609 A1 | 6/2006 | Yannas et al. |
| 2006/0122706 A1 | 6/2006 | Lo |
| 2006/0136064 A1 | 6/2006 | Sherman |
| 2006/0136065 A1 | 6/2006 | Gontarz et al. |
| 2006/0178748 A1* | 8/2006 | Dinger, III ......... A61B 17/1635 623/18.11 |
| 2006/0200250 A1 | 9/2006 | Ku |
| 2006/0206209 A1 | 9/2006 | Cragg et al. |
| 2006/0224244 A1 | 10/2006 | Thomas et al. |
| 2006/0229721 A1 | 10/2006 | Ku |
| 2006/0235541 A1 | 10/2006 | Hodorek |
| 2006/0241777 A1 | 10/2006 | Partin et al. |
| 2006/0257560 A1 | 11/2006 | Barone et al. |
| 2006/0259144 A1 | 11/2006 | Trieu |
| 2006/0282165 A1 | 12/2006 | Pisharodi |
| 2006/0282166 A1 | 12/2006 | Molz et al. |
| 2006/0287730 A1 | 12/2006 | Segal et al. |
| 2006/0293561 A1 | 12/2006 | Abay |
| 2006/0293751 A1 | 12/2006 | Lotz et al. |
| 2007/0010889 A1 | 1/2007 | Francis |
| 2007/0014867 A1 | 1/2007 | Kusanagi et al. |
| 2007/0032873 A1 | 2/2007 | Pisharodi |
| 2007/0038301 A1 | 2/2007 | Hudgins |
| 2007/0043441 A1 | 2/2007 | Pisharodi |
| 2007/0067036 A1 | 3/2007 | Hudgins et al. |
| 2007/0073402 A1 | 3/2007 | Vresilovic et al. |
| 2007/0093906 A1 | 4/2007 | Hudgins et al. |
| 2007/0106387 A1 | 5/2007 | Marcolongo et al. |
| 2007/0116678 A1 | 5/2007 | Sung et al. |
| 2007/0118218 A1 | 5/2007 | Hooper |
| 2007/0118225 A1 | 5/2007 | Hestad et al. |
| 2007/0134333 A1 | 6/2007 | Thomas et al. |
| 2007/0135922 A1 | 6/2007 | Trieu |
| 2007/0142326 A1 | 6/2007 | Shue |
| 2007/0162135 A1 | 7/2007 | Segal et al. |
| 2007/0164464 A1 | 7/2007 | Ku |
| 2007/0167541 A1 | 7/2007 | Ruberti et al. |
| 2007/0168039 A1 | 7/2007 | Trieu |
| 2007/0173951 A1 | 7/2007 | Wijlaars et al. |
| 2007/0179606 A1 | 8/2007 | Huyghe et al. |
| 2007/0179614 A1 | 8/2007 | Heinz et al. |
| 2007/0179615 A1 | 8/2007 | Heinz et al. |
| 2007/0179617 A1 | 8/2007 | Brown et al. |
| 2007/0179618 A1 | 8/2007 | Trieu et al. |
| 2007/0179620 A1 | 8/2007 | Seaton, Jr. et al. |
| 2007/0179621 A1 | 8/2007 | McClellan, III et al. |
| 2007/0179622 A1 | 8/2007 | Denoziere et al. |
| 2007/0196454 A1 | 8/2007 | Stockman et al. |
| 2007/0202074 A1 | 8/2007 | Shalaby |
| 2007/0203095 A1 | 8/2007 | Sadozai et al. |
| 2007/0203580 A1 | 8/2007 | Yeh |
| 2007/0208426 A1 | 9/2007 | Trieu |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0213825 A1 | 9/2007 | Thramann |
| 2007/0224238 A1 | 9/2007 | Mansmann et al. |
| 2007/0225823 A1 | 9/2007 | Hawkins et al. |
| 2007/0227547 A1 | 10/2007 | Trieu |
| 2007/0233135 A1 | 10/2007 | Gil et al. |
| 2007/0233259 A1 | 10/2007 | Muhanna et al. |
| 2007/0265626 A1 | 11/2007 | Seme |
| 2007/0270876 A1 | 11/2007 | Kuo et al. |
| 2007/0270970 A1 | 11/2007 | Trieu |
| 2007/0270971 A1 | 11/2007 | Trieu et al. |
| 2007/0276392 A1 | 11/2007 | Beyar et al. |
| 2007/0299540 A1 | 12/2007 | Ku |
| 2008/0004707 A1 | 1/2008 | Cragg et al. |
| 2008/0015697 A1 | 1/2008 | McLeod et al. |
| 2008/0021563 A1 | 1/2008 | Chudzik |
| 2008/0031962 A1 | 2/2008 | Boyan et al. |
| 2008/0045949 A1 | 2/2008 | Hunt et al. |
| 2008/0051889 A1 | 2/2008 | Hodorek |
| 2008/0057128 A1 | 3/2008 | Li et al. |
| 2008/0075657 A1 | 3/2008 | Abrahams et al. |
| 2008/0077242 A1 | 3/2008 | Reo et al. |
| 2008/0077244 A1 | 3/2008 | Robinson |
| 2008/0097606 A1 | 4/2008 | Cragg et al. |
| 2008/0103599 A1 | 5/2008 | Kim et al. |
| 2008/0114367 A1 | 5/2008 | Meyer |
| 2008/0125870 A1 | 5/2008 | Carmichael et al. |
| 2008/0131425 A1 | 6/2008 | Garcia et al. |
| 2008/0145404 A1 | 6/2008 | Hill et al. |
| 2008/0154372 A1 | 6/2008 | Peckham |
| 2008/0166329 A1 | 7/2008 | Sung et al. |
| 2008/0221505 A1 | 9/2008 | Betts |
| 2008/0269908 A1* | 10/2008 | Warburton ............. A61B 17/15 623/21.15 |
| 2008/0279941 A1 | 11/2008 | Boyan et al. |
| 2008/0279943 A1 | 11/2008 | Boyan et al. |
| 2009/0043398 A1 | 2/2009 | Yakimicki et al. |
| 2009/0138015 A1 | 5/2009 | Connor et al. |
| 2009/0177205 A1 | 7/2009 | McCormack et al. |
| 2009/0182421 A1 | 7/2009 | Silvestrini et al. |
| 2009/0263446 A1 | 10/2009 | Boyan et al. |
| 2010/0161073 A1 | 6/2010 | Thomas et al. |
| 2010/0198258 A1 | 8/2010 | Heaven et al. |
| 2010/0324693 A1 | 12/2010 | Hardenbrook |
| 2010/0324694 A1 | 12/2010 | Hassler et al. |
| 2011/0040332 A1 | 2/2011 | Culbert et al. |
| 2011/0172771 A1 | 7/2011 | Boyan et al. |
| 2011/0208305 A1 | 8/2011 | Malinin |
| 2011/0270400 A1 | 11/2011 | Kita et al. |
| 2011/0318704 A1 | 12/2011 | Teichmann |
| 2012/0022568 A1 | 1/2012 | Koblish et al. |
| 2012/0053642 A1 | 3/2012 | Lozier et al. |
| 2012/0203346 A1 | 8/2012 | Kraus |
| 2013/0006368 A1 | 1/2013 | Walsh et al. |

(56) References Cited

U.S. PATENT DOCUMENTS

| | | |
|---|---|---|
| 2013/0211451 A1 | 8/2013 | Wales et al. |
| 2014/0214080 A1 | 7/2014 | Wales et al. |
| 2014/0324169 A1 | 10/2014 | Maher et al. |
| 2015/0351815 A1 | 12/2015 | Wales et al. |
| 2016/0038308 A1 | 2/2016 | Walsh et al. |
| 2016/0287392 A1 | 10/2016 | Patrick et al. |
| 2016/0302930 A1 | 10/2016 | Axelrod et al. |
| 2017/0165074 A1 | 6/2017 | Walsh et al. |
| 2017/0304039 A1 | 10/2017 | Eaves, III et al. |
| 2018/0185159 A1 | 7/2018 | Patrick et al. |

FOREIGN PATENT DOCUMENTS

| | | |
|---|---|---|
| EP | 0222407 A2 | 5/1987 |
| EP | 0346129 A1 | 12/1989 |
| EP | 0505634 A1 | 9/1992 |
| EP | 0410010 B1 | 10/1993 |
| EP | 0411105 B1 | 6/1995 |
| EP | 0845480 A1 | 6/1998 |
| EP | 0919209 A1 | 6/1999 |
| EP | 1287796 A1 | 3/2003 |
| EP | 1030697 B1 | 8/2003 |
| EP | 1344538 A1 | 9/2003 |
| EP | 1584338 A2 | 10/2005 |
| EP | 1482996 B1 | 11/2005 |
| GB | 02056882 A | 3/1981 |
| GB | 02128501 A | 5/1984 |
| JP | 02-184580 | 7/1990 |
| JP | 04053843 | 2/1992 |
| JP | 07247365 | 9/1995 |
| JP | 11035732 | 2/1999 |
| JP | 2005-199054 | 7/2005 |
| JP | 2006-101893 | 4/2006 |
| WO | WO90/007545 A2 | 7/1990 |
| WO | WO90/007575 A1 | 7/1990 |
| WO | WO90/010018 A1 | 9/1990 |
| WO | WO93/016664 A1 | 9/1992 |
| WO | WO94/001483 A1 | 1/1994 |
| WO | WO95/025183 A1 | 9/1995 |
| WO | WO97/006101 A1 | 2/1997 |
| WO | WO97/046178 A1 | 12/1997 |
| WO | WO98/002146 A2 | 1/1998 |
| WO | WO98/050017 A1 | 11/1998 |
| WO | WO99/025391 A2 | 5/1999 |
| WO | WO99/034845 A1 | 7/1999 |
| WO | WO00/030998 A1 | 6/2000 |
| WO | WO00/042991 A1 | 7/2000 |
| WO | WO00/062829 A1 | 10/2000 |
| WO | WO00/066191 | 11/2000 |
| WO | WO01/002033 A1 | 1/2001 |
| WO | WO01/022902 A2 | 4/2001 |
| WO | WO01/059160 A1 | 8/2001 |
| WO | WO01/064030 A1 | 9/2001 |
| WO | WO01/070436 A1 | 9/2001 |
| WO | WO01/091822 A1 | 12/2001 |
| WO | WO02/009647 A2 | 2/2002 |
| WO | WO02/030480 A1 | 4/2002 |
| WO | WO02/064182 A3 | 8/2002 |
| WO | WO03/030787 A1 | 4/2003 |
| WO | WO03/092760 A1 | 11/2003 |
| WO | WO04/060554 A1 | 7/2004 |
| WO | WO04/101013 A1 | 11/2004 |
| WO | WO05/077013 A2 | 8/2005 |
| WO | WO05/077304 A1 | 8/2005 |
| WO | WO05/097006 A2 | 10/2005 |
| WO | WO06/018531 A2 | 2/2006 |
| WO | WO06/019634 A1 | 2/2006 |
| WO | WO06/030054 A1 | 3/2006 |
| WO | WO06/034365 A2 | 3/2006 |
| WO | WO 2006/060416 | 6/2006 |
| WO | WO 2012/162552 | 11/2012 |

OTHER PUBLICATIONS

Ariga et al., "Immobilization of Microorganisms with PVA Hardened by Iterative Freezing and Thawing," Journal of Fermentation Technology, 65(6): pp. 651-658 (1987).

Boyan et al., "Effect of Titanium Surface Characteristics on Chondrocytes and Osteoblasts in Vitro," Cells and Materials, vol. 5, No. 4, pp. 323-335 (1995).

Boyan et al., "Osteoblast-Mediated Mineral Deposition in Culture is Dependent on Surface Microtopography," Calcif. Tissue Int., 71:519-529 (2002).

Bray et al., Poly(vinyl alcohol) Hydrogels for Synthetic Articular Cartilage Material, M. Biomed. Mater. Res., vol. 7, pp. 431-443.

Brunette, "The Effects of Implant Surface Topography on the Behavior of Cells," Int. J. Oral Maxillofac Implants, 3:231-240 (1988).

Chen et al., "Boundary layer infusion of heparin prevents thrombosis and reduces neointimal hyperplasia in venous polytetrafluoroethylene grafts without system anticoagulation," J. Vascular Surgery, 22:237-247 (1995).

Chu et al., "Polyvinyl Alcohol Cryogel: An Ideal Phantom Material for MR Studies of Arterial Elasticity," Magnetic Resonance in Medicine, v. 37, pp. 314-319 (1997).

Hickey et al., "Mesh size and diffusive characteristics of semicrystalline poly(vinyl alcohol) membranes prepared by freezing/thawing techniques," Journal of Membrane Science, 107(3), pp. 229-237 (1995).

Hoffman et al., "Interactions of Blood and Blood Components at Hydrogel Interfaces," Ann. New York Acad. Sci., 283:372-382 (1977).

Hunt, Knee Simulation, Creep, and Friction Tests of Poly(Vinyl Alcohol) Hydrogels Manufactured Using Injection Molding and Solution Casting, Thesis for M.S., University of Notre Dame (Jul. 2006).

Katta et al., "Friction and wear behavior of poly(vinyl alcohol)/poly(vinyl pyrrolidone) hydrogels for articular cartilage replacement," Journal of Biomedical Materials Research, vol. 83A, pp. 471-479 (2007).

Kieswetter et al., "The Role of Implant Surface Characteristics in the Healing of Bone," Crit. Rev. Oral Biol. Med., 7(4):329-345 (1996).

Kieswetter et al., "Surface roughness modulates the local production of growth factors and cytokines by osteoblast-like MG-63 cells," Journal of Biomedical Materials Research, vol. 32, pp. 55-63 (1996).

Kobayashi et al., "Characterization of a polyvinyl alcohol-hydrogel artificial articular cartilage prepared by injection molding," J. Biomater. Sci. Polymer Edn., 15(6): 741-751 (2003).

Kobayashi et al., "Development of an artificial meniscus using polyvinyl alcohol-hydrogel for early return to, and continuance of, athletic life in sportspersons with severe meniscus injury. I: mechanical evaluation." The Knee, 10 (2003); 47-51.

Kohavi et al., "Markers of primary mineralization are correlated with bone-bonding ability of titanium or stainless steel in vivo," Clin. Oral. Impl. Res., 6:1-13 (1995).

Koutsopoulos et al., "Calcification of porcine and human cardiac valves: testing of various inhibitors for antimineralization," J. Mater. Sci. Mater. Med., 9:421-424 (1998).

Kwak, BK, et al., "Chitin-based Embolic Materials in the Renal Artery of Rabbits: Pathologic Evaluation of an Absorbable Particulate Agent", Radiology, 236:151-158 (2005).

Landolt et al., "Electrochemical micromachining, polishing and surface structuring of metals: fundamental aspects and new developments", Elsevier Science Ltd., pp. 3185-3201 (2003).

Lazzeri et al., "Physico-chemical and mechanical characterization of hydrogels of poly(vinyl alcohol) and hyaluronic acid," J. Mater. Sci. in Med., 5:862-867 (1994).

Liao et al., "Response of rat osteoblast-like cells to microstructured model surfaces in vitro," Biomaterials, 24, pp. 649-654 (2003).

Lozinsky et al., "Study of cryostructurization of polymer systems. VII. Structure formation under freezing of poly(vinyl alcohol) acqueous solutions," Colloid & Polymer Science, vol. 264, pp. 19-24 (1986).

(56) References Cited

OTHER PUBLICATIONS

Lozinsky et al., "Study of Cryostructuration of Polymer Systems. XII. Poly(vinyl alcohol) Cryogels: Influence of Low-Molecular Electrolytes," Journal of Applied Polymer Science, vol. 61, pp. 1991-1998 (1996).

Lozinsky et al., "Study of Cryostructuration of Polymer Systems. XI. The Formation of PVA Cryogels by Freezing-Thawing the Polymer Aqueous Solutions Containing Additives of Some Polyols," Journal of Applied Polymer Science, vol. 58, pp. 171-177 (1995).

Lozinsky et al., "Poly(vinyl alcohol) cryogels employed as matrices for cell immobilization. 2. Entrapped cells resemble porous fillers in their effects on the properties of PVA-cryogel carrier," Enzyme and Microbial Technology, vol. 20, No. 3, pp. 182-190 (1997).

Lozinsky et al., "Poly(vinyl alcohol) cryogels employed as matrices for cell immobilization. 3. Overview of recent research and developments," Enzyme and Microbial Technology, vol. 23, No. 3-4, pp. 227-242 (1998).

Lusta et al., "Immobilization of fungus *Aspergillus* sp. by a novel cryogel technique for production of extracellular hydrolytic enzymes", Process Biochemistry, vol. 35, pp. 1177-1182 (2000).

Ma et al., "Friction Properties of novel PVP/PVA blend hydrogels as artificial cartilage," Journal of Biomedical Materials Research, vol. 93A, pp. 1016-1019 (2010).

Martin et al., "Effect of titanium surface roughness on proliferation, differentiation, and protein synthesis of human osteoblast-like cells (MG63)," Journal of Biomedical Materials Research, vol. 29, pp. 389-401 (1995).

Nagura et al., "Structure of poly(vinyl alcohol) hydrogel prepared by repeated freezing and melting," Polymer, 30:762-765 (1989).

Nakashima et al., "Study on Wear Reduction Mechanisms of Artificial Cartilage by Synergistic Protein Boundary Film Formation," Japan Soc'y of Mech. Eng'r Int'l J., Series C, vol. 48, No. 4, pp. 555-561 (2005).

Oka et al., "Development of an Artificial Articular Cartilage", Clinical Materials, vol. 6, pp. 361-381 (1990).

Ong et al., "Osteoblast Responses to BMP-2-Treated Titanium in Vitro," The International Journal of Oral & Maxillofacial Implants, vol. 12, No. 5, pp. 649-654 (1997).

Peppas et al., "Reinforced uncrosslinked poly(vinyl alcohol) gels produced by cyclic freezing-thawing processes: a short review," Journal of Controlled Release, 16(3): 305-310 (1991).

Peppas et al., "Structure of Hydrogels by Freezing-Thawing Cyclic Processing," Bulletin of the American Physical Society, 36:582 (1991).

Peppas et al., "Controlled release from poly(vinyl alcohol) gels prepared by freezing-thawing processes," Journal of Controlled Release, vol. 18, pp. 95-100 (1992).

Peppas et al., "Ultrapure poly(vinyl alcohol) hydrogels with mucoadhesive drug delivery characteristics," European Journal of Pharmaceutics and Biopharmaceutics, 43(1): 51-58 (1997).

Ratner et al., Biomaterials Science an Introduction to Materials in Medicine, Academic Press, pp. 52, 53, & 62 (1996).

Ricciardi et al., "Structure and Properties of Poly(vinyl alcohol) Hydrogels Obtained by Freeze/Thaw Techniques," Macromol. Symp., 222: 49-63 (2005).

Schwartz et al., "Underlying Mechanisms at the Bone-Biomaterial Interface," Journal of Cellular Biochemistry, 56:340-347 (1994).

Singh et al., "Polymeric Hydrogels: Preparation and Biomedical Applications," J. Sci. Ind. Res., 39:162-171 (1980).

Stauffer et al., "Poly(vinyl alcohol) hydrogels prepared by freezing-thawing cyclic processing," Polymer 33(1818):3932-3936 (1992).

Stewart et al., "Protein release from PVA gels prepared by freezing and thawing techniques," Proc. Int. Symp. Controlled Release Bioact. Mater., $26^{th}$, 1004-1005 (1999).

Szczesna-Antezak et al., "*Bacillus subtilis* cells immobilised in PVA-cryogels," Biomolecular Engineering, vol. 17, pp. 55-63 (2001).

The American Heritage® Science Dictionary [online], Houghton Mifflin Company, 2002 [retrieved on Jun. 3, 2008]. Retrieved from the internet: <URL: http://dictionary.reference.com/browse/pore>.

Watase et al., "Rheological and DSC Changes in Poly(vinyl alcohol) Gels Induced by Immersion in Water," Journal of Polymer Science, Polym. Phys. Ed, 23(9): 1803-1811 (1985).

Watase et al., "Thermal and rheological properties of poly(vinyl alcohol) hydrogels prepared by repeated cycles of freezing and thawing," Makromol. Chem., v. 189, pp. 871-880 (1988).

Willcox et al., "Microstructure of Poly(vinyl alcohol) Hydrogels Produced by Freeze/Thaw Cycling," Journal of Polymer Sciences: Part B: Polymer Physics, vol. 37, pp. 3438-3454 (1999).

WordNet® 3.0 [online], Princeton University, 2006 [retrieved on Aug. 6, 2008]. Retrieved from the Internet: <URL: http://dictionary.reference.com/browse/mesh>.

Yamaura et al., "Properties of Gels Obtained by Freezing/Thawing of Poly(vinyl Alcohol)/Water/Dimethyl Sulfoxide Solutions," J. Appl. Polymer Sci., 37:2709-2718 (1989).

Yokoyama et al., "Morphology and structure of highly elastic poly(vinyl alcohol) hydrogel prepared by repeated freezing-and-melting", Colloid & Polymer Science, vol. 264, No. 7, pp. 595-601 (1986).

Zheng-Qiu et al., "The development of artificial articular cartilage—PVA-hydrogel," Bio-Medical Materials and Engineering, vol. 8, pp. 75-81 (1998).

Extended European Search Report issued in connection with European Patent Application No. 19213121.7, dated Feb. 26, 2020, 6 pages.

\* cited by examiner

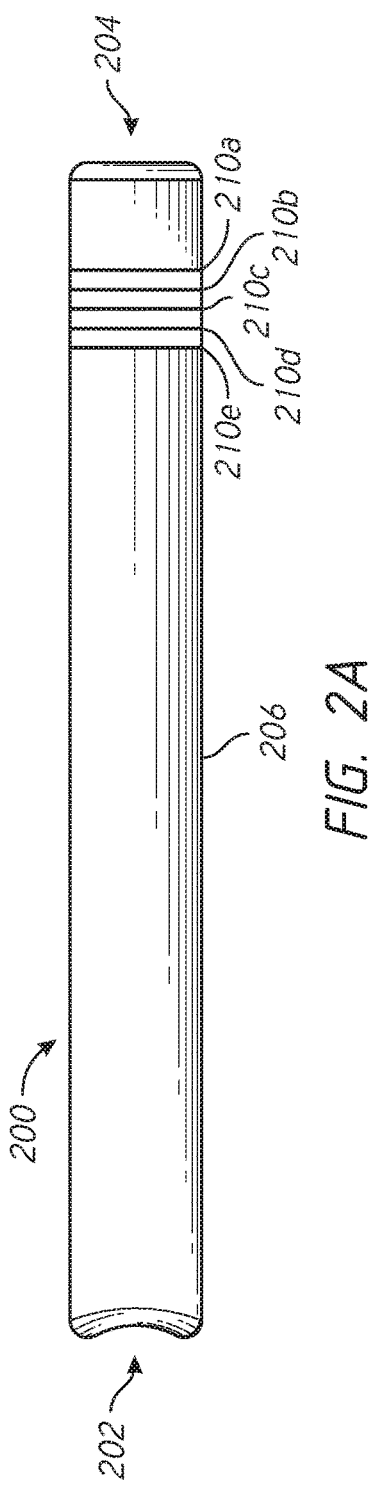
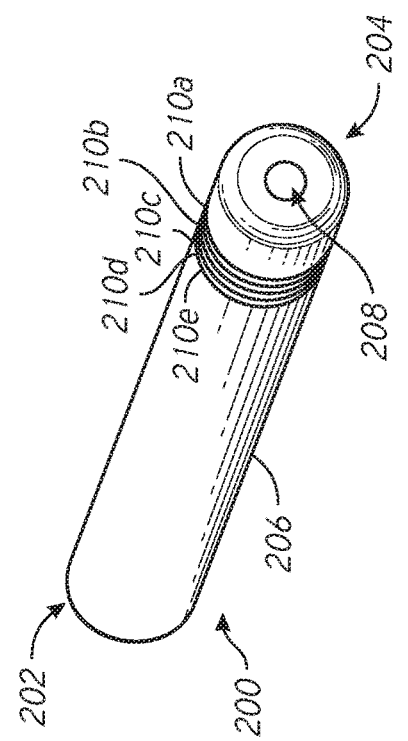
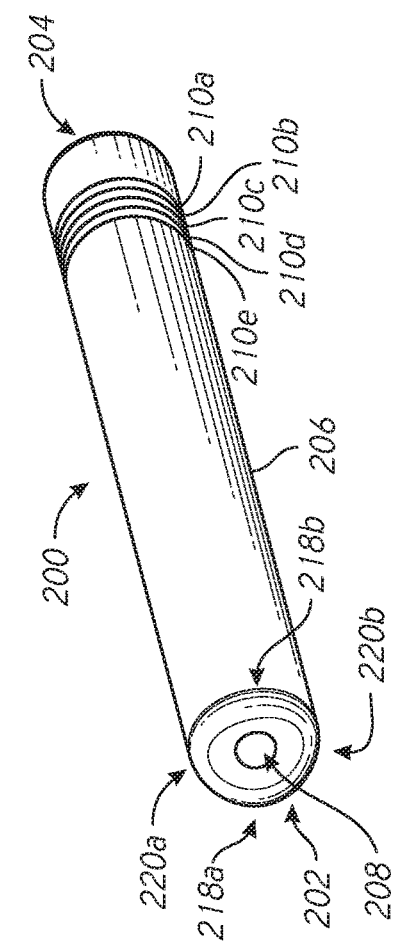
FIG. 2A
FIG. 2B
FIG. 2C

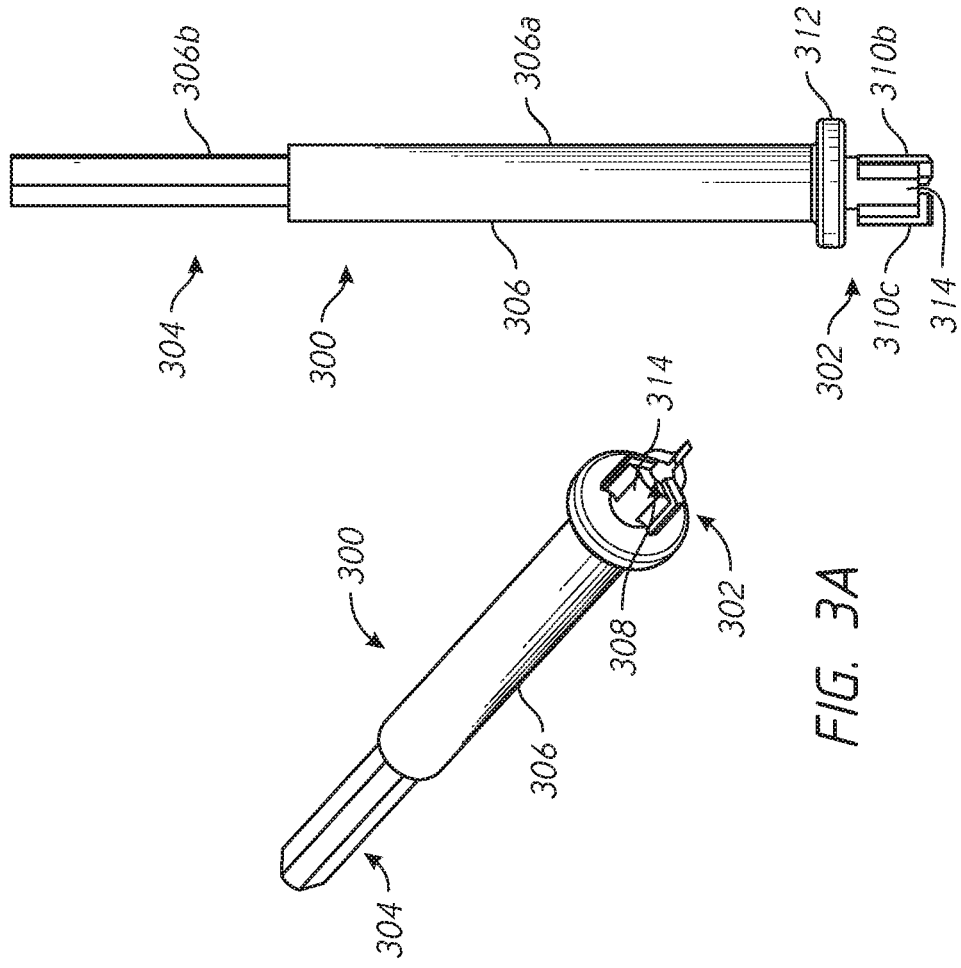

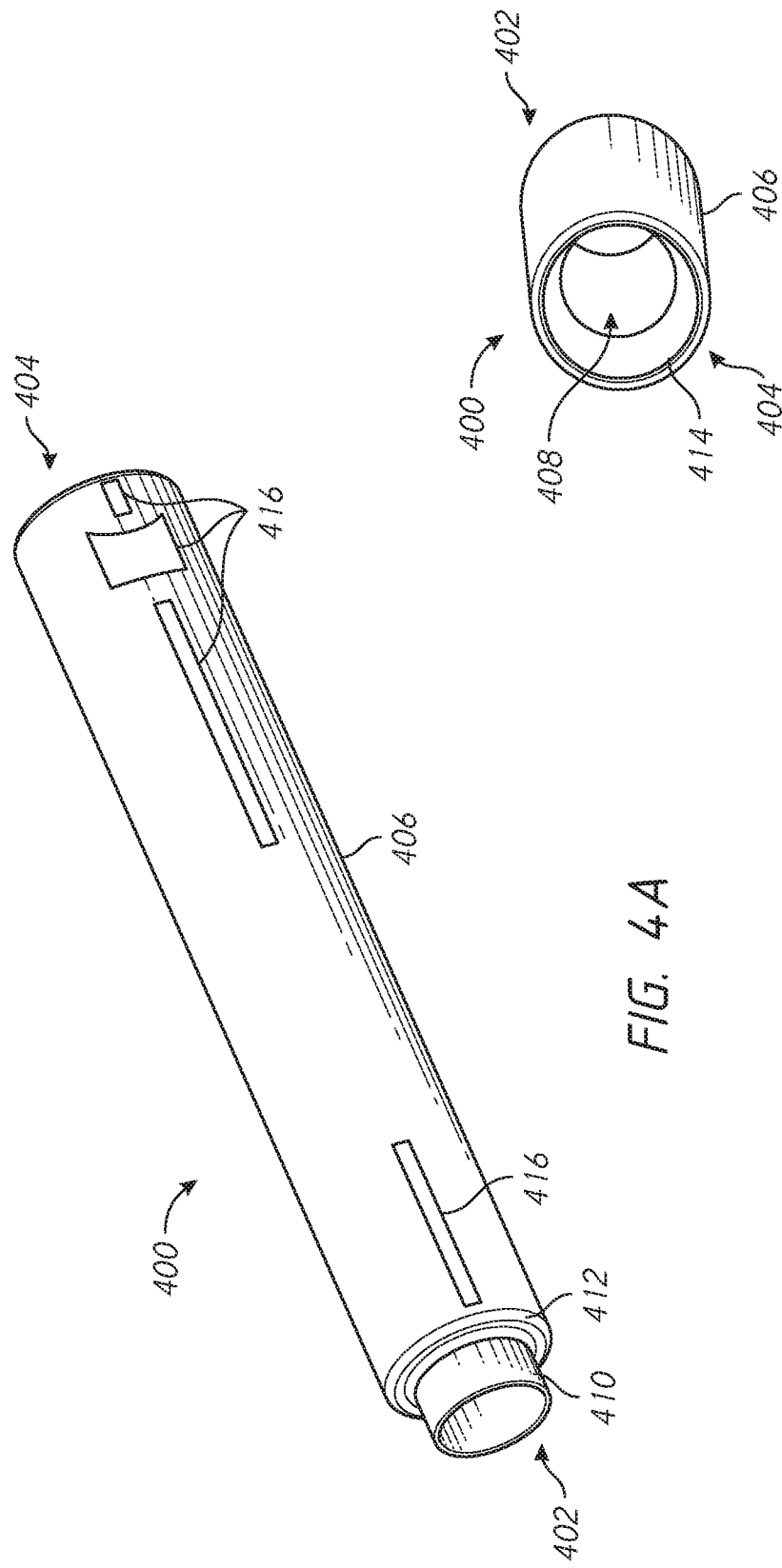

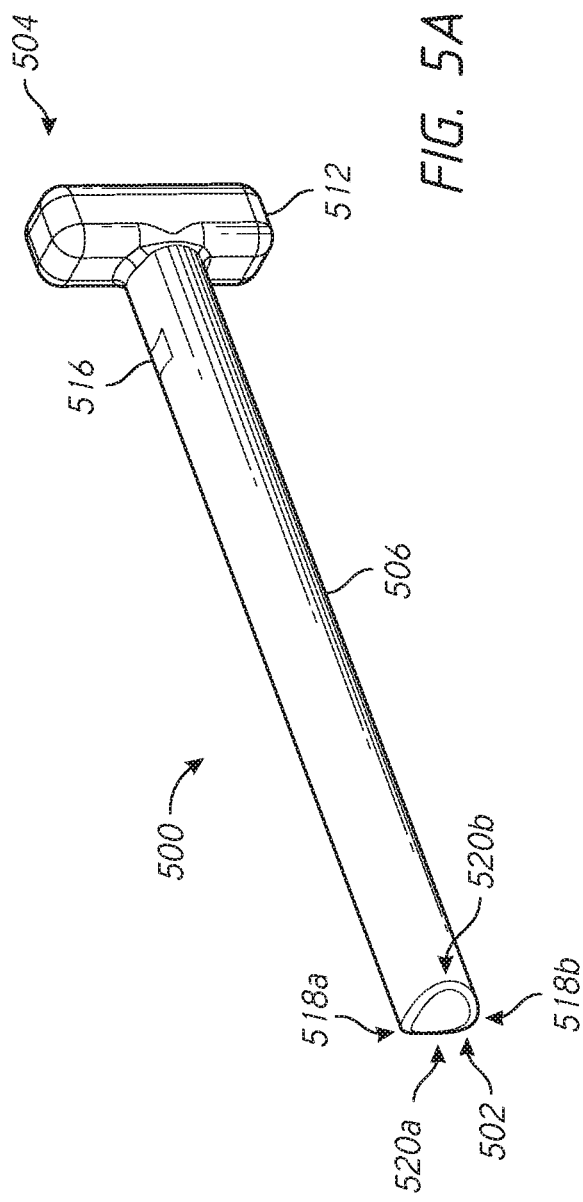
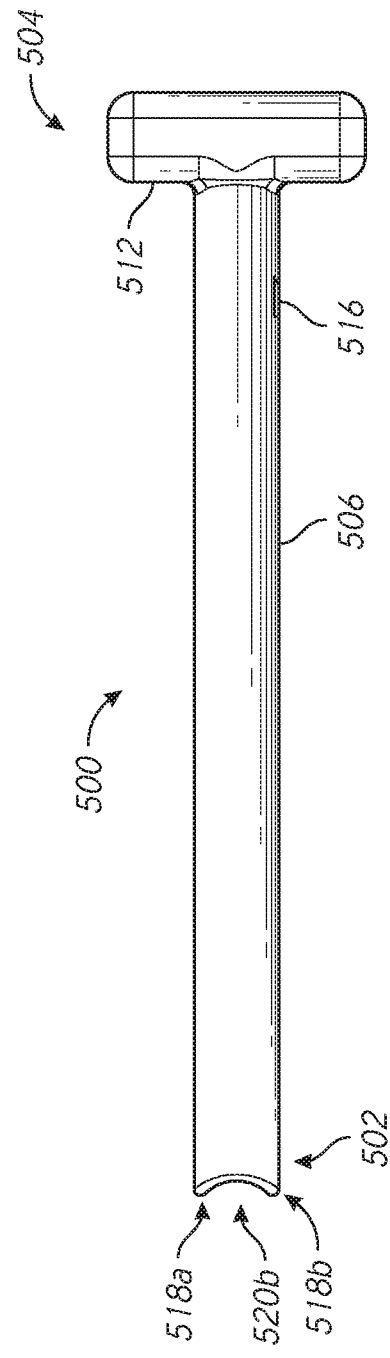

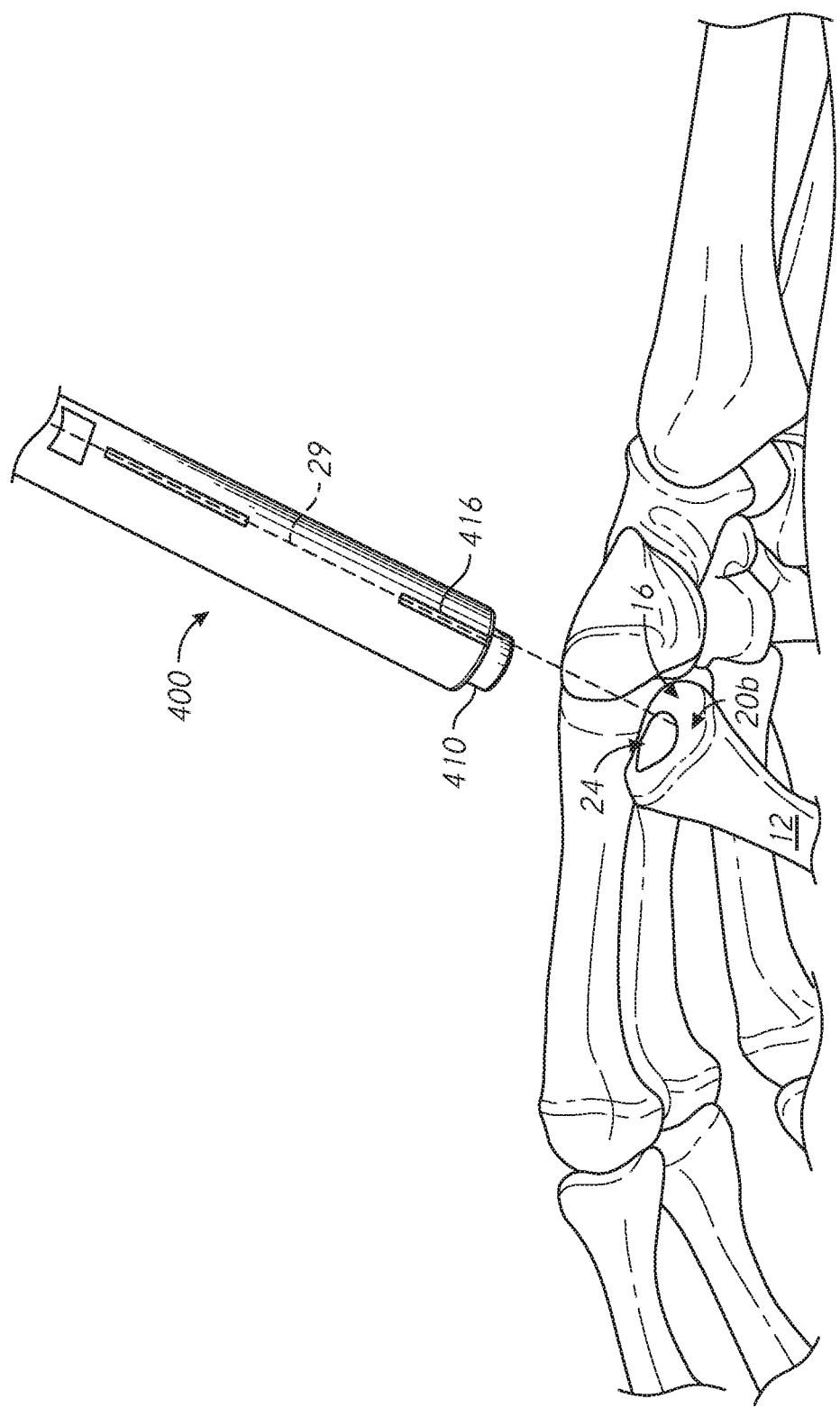

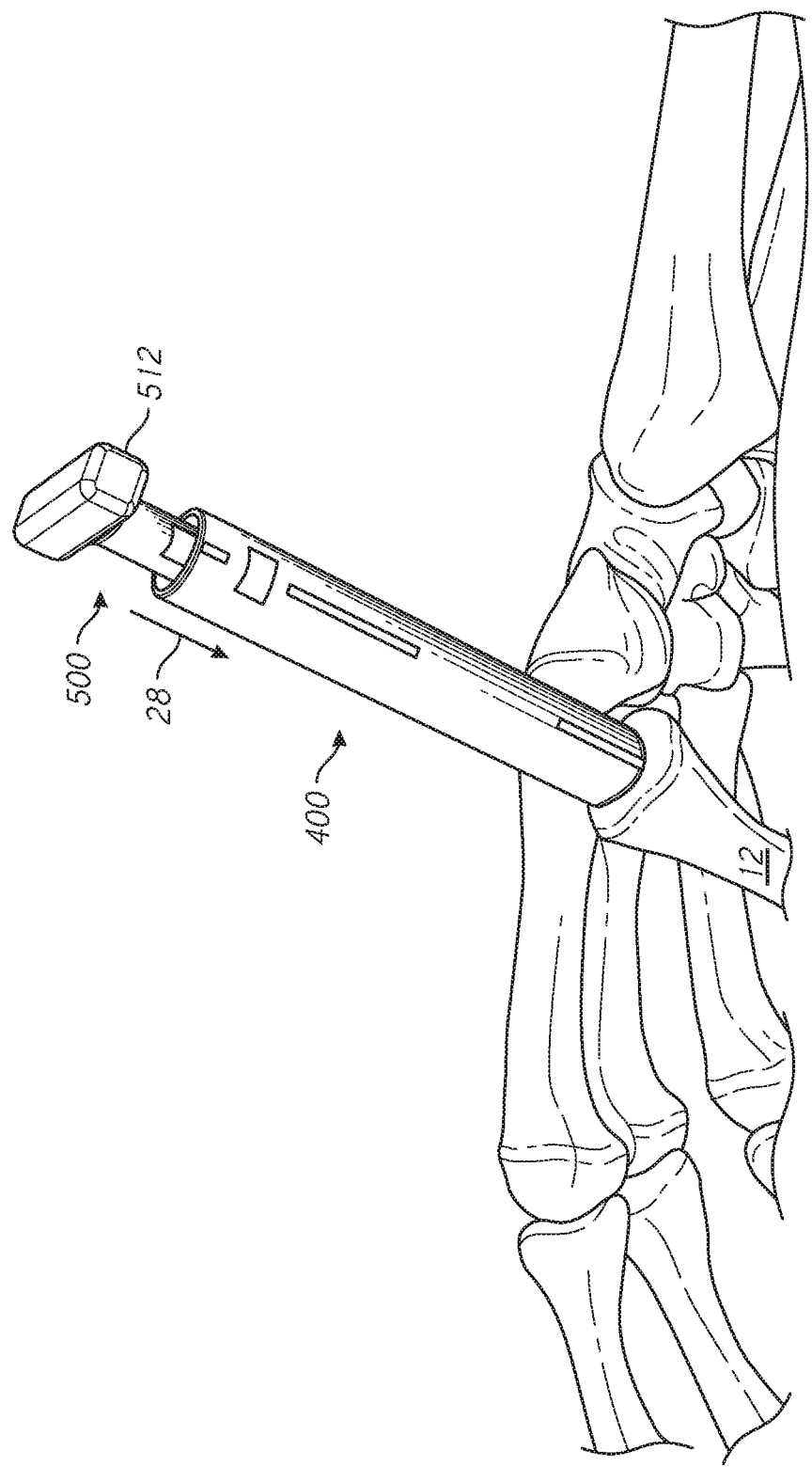

CARPOMETACARPAL (CMC) IMPLANTS AND METHODS

INCORPORATION BY REFERENCE TO ANY PRIORITY APPLICATIONS

The present application claims priority benefit of U.S. Provisional Patent App. No. 62/141,186, filed on Mar. 31, 2015.

Any and all applications for which a foreign or domestic priority claim is identified in the Application Data Sheet as filed with the present application are hereby incorporated by reference under 37 C.F.R. § 1.57 for all purposes.

BACKGROUND

Field

This disclosure relates generally to implants, and, more specifically, to hydrogel joint implants and various tools, devices, systems, and methods related thereto.

Description of Related Art

Implants can be used to replace deteriorated or otherwise damaged cartilage within a joint. Such devices can be used to treat osteoarthritis, rheumatoid arthritis, other inflammatory diseases, generalized joint pain, joints damaged in an accident, joints damaged while participating in athletics, joints damaged due to repetitive use, and/or other joint diseases.

SUMMARY

In some embodiments, an implant comprises, or alternatively consists essentially of, a hydrogel body comprising an upper surface, a planar lower surface opposite the upper surface, and sidewalls extending between the upper surface and the lower surface. The upper surface comprises a saddle shape. The sadly shape includes a first peak, a second peak, a first trough, and a second trough. The first trough is laterally between the first peak and the second peak. The second trough is laterally between the first peak and the second peak. The first peak is laterally between the first trough and the second trough. The second peak is laterally between the first trough and the second trough.

The hydrogel may comprise polyvinyl alcohol (PVA). The hydrogel may comprise water. The hydrogel may comprise saline. The upper surface may be contoured to correspond to an outer surface of a trapezium. The body may have a diameter between 4 mm and 8 mm. The implant may be load bearing. The implant may be non-biodegradable. The implant may be configured to be placed in a carpometacarpal joint. The lower surface may be configured to be placed in a cavity in a first metacarpal bone. The upper surface may be configured to abut a trapezium. A distance between at least one of the first peak and the second peak and the planar lower surface may be between 10% and 20% greater than a distance between at least one of the first trough and the second trough and the planar lower surface.

In some embodiments, a placer comprises, or alternatively consists essentially of, a first end, a second end opposite the first end, and a body extending between the first end and the second end. The first end comprises a saddle shape. The saddle shape includes a first peak, a second peak, a first trough, and a second trough. The first trough is laterally between the first peak and the second peak. The second trough is laterally between the first peak and the second peak. The first peak is laterally between the first trough and the second trough. The second peak is laterally between the first trough and the second trough.

The placer may further comprise a lumen extending through the body from the first end to the second end. The lumen may be configured to facilitate placement of a guide pin. The placer may further comprise a measurement band proximate to the second end. The measurement band may comprise a plurality of measurement bands spaced by 1 mm. The first end may be contoured to correspond to an outer surface of a first metacarpal bone.

In some embodiments, a drill bit comprises, or alternatively consists essentially of, a distal end, a proximal end opposite the distal end, and a body extending between the distal end and the proximal end. The distal end comprises a flange and a plurality of cutters distal to the flange. The flange has a lateral dimension greater than a lateral dimension of the body. The proximal end is configured to be coupled to a drill.

The plurality of cutters may comprise three cutters. The plurality of cutters may be spaced 120° from each other. Each of the plurality of cutters may extend from a hub. The drill bit may further comprise a lumen extending through the body from the proximal end to the distal end. The lumen may be configured to be tracked over a guide pin. The proximal end may comprise a polygonal lateral cross-section.

In some embodiments, an introducer comprises, or alternatively consists essentially of, a distal end, a proximal end opposite the distal end, and a body extending between the distal end and the proximal end. The distal end comprises a neck portion. The body is coupled to the neck portion at a shoulder. The body comprises a lumen including a flared shape proximate to the proximal end.

The body may comprise alignment indicia. The body may be cylindrical.

In some embodiments, a plunger comprises, or alternatively consists essentially of, a distal end, a proximal end opposite the distal end, and a body extending between the distal end and the proximal end. The distal end comprises a saddle shape. The saddle shape includes a first peak, a second peak, a first trough, and a second trough. The first trough is laterally between the first peak and the second peak. The second trough is laterally between the first peak and the second peak. The first peak is laterally between the first trough and the second trough. The second peak is laterally between the first trough and the second trough. The proximal end comprises a head portion.

The distal end may be configured to abut an end surface of an implant contoured to abut a trapezium. The body may comprise alignment indicia. The head portion may comprise a T-shaped handle. The body may comprise alignment indicia. The body may be cylindrical.

In some embodiments, a deployment system comprises, or alternatively consists essentially of, the introducer and the plunger.

The body of the plunger may be configured to extend at least partially through the lumen of the introducer. The plunger may be configured distally advance an implant through the lumen of the introducer. The plunger may be radially inwardly compress an implant in the lumen of the introducer. The plunger may be configured deploy an implant out of the distal end of the introducer.

In some embodiments, a kit comprises, or alternatively consists essentially of, at least two of the placer, the drill bit, the introducer, the plunger, and a guide pin.

The kit may further comprise the implant.

In some embodiments, a method of positioning an implant in a carpometacarpal joint comprises, or alternatively consists essentially of, aligning an implant deployment system with a recess in a carpometacarpal bone. The carpometacarpal bone comprises the first metacarpal bone. The joint comprises a surface of a trapezium. The recess faces a carpometacarpal joint. The implant deployment system comprises an introducer comprising first alignment indicia and a plunger comprising second alignment indicia. The method further comprises deploying the implant out of the implant deployment system partially and partially into the recess. The implant comprises a contoured upper surface contoured to abut the surface of the trapezium. The contoured upper surface comprises a first peak, a second peak, a first trough laterally between the first peak and the second peak, and a second trough laterally between the first peak and the second peak. The first peak is laterally between the first trough and the second trough. The second peak is laterally between the first trough and the second trough. After deployment, the implant is 1 mm to 3 mm proud.

Aligning the implant deployment system may comprise aligning the first alignment indicia with a surface feature of the carpometacarpal bone. The method may further comprise loading the implant in the implant deployment system. Loading the implant may comprise aligning the contoured upper surface of the implant with at least one of the first alignment indicia and the second alignment indicia. The method may further comprise radially compressing the implant in the implant deployment system by distally urging the implant through a lumen of the introducer using the plunger.

In some embodiments, a method of positioning an implant in a carpometacarpal joint comprises, or alternatively consists essentially of, aligning an implant deployment system with a recess in a carpometacarpal bone and deploying the implant out of the implant deployment system partially and partially into the recess. The recess faces a carpometacarpal joint. The implant comprises a contoured upper surface.

The carpometacarpal bone may comprise the first metacarpal bone. The joint may comprise a surface of a trapezium. The upper surface of the implant may be contoured to abut the surface of the trapezium. An introducer of the implant deployment system may comprise alignment indicia. Aligning the implant deployment system may comprise aligning the alignment indicia with a surface feature of the carpometacarpal bone. Aligning the implant deployment system may comprise positioning neck portion of an introducer of the implant deployment system at least partially in the recess. Aligning the implant deployment system may comprise abutting a shoulder of an introducer of the implant deployment system against a surface of the carpometacarpal bone. The implant may comprise one of the implants described above. After deployment, the implant may be 1 mm to 3 mm proud. The deployment system may comprise one of the introducers described above. The deployment system may comprise one of the plungers described above. The deployment system may comprise one of the deployment systems described above. The method may further comprise loading the implant in the implant deployment system. Loading the implant may comprise aligning the implant in the implant deployment system. An introducer of the implant deployment system may comprise alignment indicia. A plunger of the implant deployment system may comprise alignment indicia. A plunger of the implant deployment system may comprise a contoured distal end. The method may further comprise radially compressing the implant in the implant deployment system. Radially compressing the implant in the implant deployment system may comprise distally urging the implant through a lumen of an introducer of the implant deployment system using a plunger of the implant deployment system. The lumen of the introducer of the implant deployment system may comprise a flared shape. Deploying the implant may comprise urging the implant through a lumen of an introducer of the implant deployment system using a plunger of the implant deployment system. Deploying the implant may be manual. Deploying the implant may comprise distally advancing a head portion of a plunger. Deploying the implant may be mechanically assisted. The method may further comprise forming an incision proximate to the carpometacarpal joint. The method may further comprise moving the carpometacarpal bone to expose the carpometacarpal joint. The method may further comprise tamping a guide pin in the carpometacarpal bone. Tamping the guide pin may comprise using a placer. The placer may comprise one of the placers described above. The method may further comprise, before deploying the implant, removing the guide pin. The method may further comprise forming the recess in the carpometacarpal bone. Forming the recess in the carpometacarpal bone may comprise using a drill bit. Using the drill bit may comprise tracking the drill bit over a guide pin. The drill bit may comprise one of drill bits described above. The drill bit may comprise a flange. Forming the recess in the carpometacarpal bone may comprise abutting a surface of in the carpometacarpal bone with the flange. The method may further comprise measuring a depth of the recess in the carpometacarpal bone. Measuring the recess may comprise using an end of a placer comprising measurement bands. Measuring the recess may comprise comparing a feature of a surface of the carpometacarpal bone to the measurement bands. The feature of the surface of the carpometacarpal bone may comprise a peak. The feature of the surface of the carpometacarpal bone may comprise a trough. Measuring the recess may comprise comparing a lateral dimension of the recess in the carpometacarpal bone to a lateral dimension of a placer. The placer may comprise one of placers described above. The method may further comprise, after measuring the recess, increasing at least one of a depth and a diameter of the recess. The method may further comprise, after deploying the implant, moving the carpometacarpal bone to close the carpometacarpal joint.

The carpometacarpal bone may comprise the first metacarpal bone. The joint may comprises a surface of a trapezium. The upper surface of the implant may be contoured to abut the surface of the trapezium. An introducer of the implant deployment system may comprise alignment indicia. Aligning the implant deployment system may comprise aligning the alignment indicia with a surface feature of the carpometacarpal bone. The upper surface of the implant may comprise a first peak, a second peak, a first trough laterally between the first peak and the second peak, a second trough. The second trough may be laterally between the first peak and the second peak, the first peak may be laterally between the first trough and the second trough, and the second peak may be laterally between the first trough and the second trough. After deployment, the implant may be 1 mm to 3 mm proud. The implant deployment system may comprise an introducer comprising first alignment indicia and a plunger comprising second alignment indicia. Loading the implant may comprise aligning the contoured upper surface of the implant with at least one of the first alignment indicia and the second alignment indicia. The method may further comprise radially compressing the implant in the implant deployment system by distally urging the implant through a lumen of an introducer of the implant deployment system using a plunger of the implant deployment system. The method may further comprise tamping a guide pin in the carpometacarpal bone using a placer. The method may further comprise forming the recess in the carpometacarpal bone using a drill bit.

BRIEF DESCRIPTION OF THE DRAWINGS

Certain features, aspects, and advantages of the disclosure are described with reference to drawings, which are intended to illustrate, but not to limit, the various inventions disclosed herein. It is to be understood that the attached drawings are for the purpose of illustrating concepts and embodiments of the disclosure and may not be to scale.

FIG. 2A is a side perspective view of an example placer.

FIG. 2B is a first end and side perspective view of the placer of FIG. 2A.

FIG. 2C is a second end and side perspective view of the placer of FIG. 2A.

FIG. 3A is a side and bottom perspective view of an example drill bit.

FIG. 3B is a side perspective view of the drill bit of FIG. 3A.

FIG. 3C is a bottom plan view of the drill bit of FIG. 3A.

FIG. 3D is a top and side perspective view of the drill bit of FIG. 3A.

FIG. 4A is a side and bottom perspective view of an example introducer.

FIG. 4B is a side and top perspective view of the introducer of FIG. 4A.

FIG. 5A is a side and bottom perspective view of an example plunger.

FIG. 5B is a side perspective view of the plunger of FIG. 5A.

DETAILED DESCRIPTION

Figure 1B:
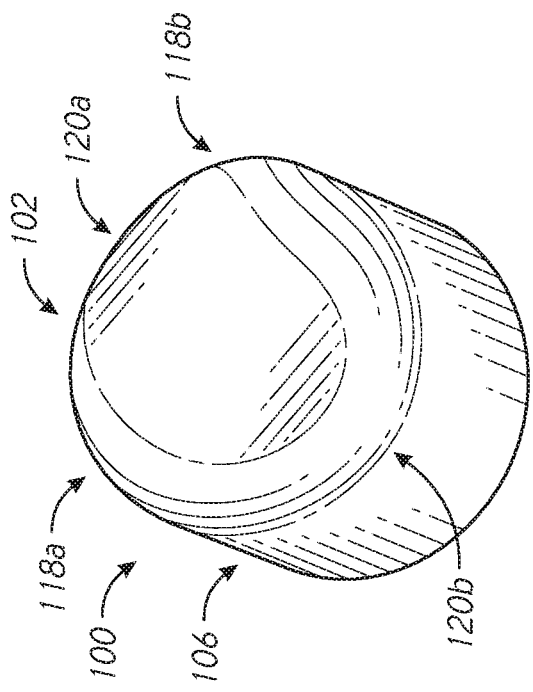
FIG. 1B is a top and side perspective view of the implant of FIG. 1A.

The discussion and the figures illustrated and referenced herein describe various embodiments of a cartilage implant, as well as various tools, systems, and methods related thereto. A number of these devices and associated treatment methods are particularly well suited to replace deteriorated or otherwise damaged cartilage within a joint. Such implants are configured to remain within the patient's joint on a long-term basis (e.g., for most or all of the life of the patient or subject), and, as such, are configured, in some embodiments, to replace native cartilage. In some embodiments, an implant is configured to be substantially non-biodegradable and/or non-erodable. In some embodiments, an implant is configured to remain within the patient's joint or other portion of the anatomy for a minimum of 10 years, up to 100 years (e.g., about 10 years, about 20 years, about 25 years, about 30 years, about 35 years, about 40 years, about 45 years, about 50 years, about 55 years, about 60 years, about 65 years, about 70 years, about 75 years, about 80 years, about 85 years, about 90 years, about 95 years, about 100 years, duration ranges between the foregoing values, etc.) without losing structural and/or physical properties and/or without losing ability to function as a cartilage replacement component or device. In some embodiments, an implant is configured to remain within the anatomy for greater than 100 years without losing structural and/or physical properties and/or without losing ability to function as a cartilage replacement component. Certain implants described herein can be used to treat osteoarthritis, rheumatoid arthritis, other inflammatory diseases, generalized joint pain, joints damaged in an accident, joints damaged while participating in athletics, joints damaged due to repetitive use, and/or other joint diseases. However, the various devices, systems, methods, and other features of the embodiments disclosed herein may be utilized or applied to other types of apparatuses, systems, procedures, and/or methods, including arrangements that have non-medical benefits or applications.

Certain embodiments described herein may be advantageous because they include one, several, or all of the following benefits: (i) improved treatment of the carpometacarpal joint; (ii) improved coupling of disparate implant materials; (iii) improved cavity wall apposition; (iv) improved implant site preparation tooling and/or systems; (v) improved implant site preparation methods; (vi) improved implant deployment tooling and/or systems; and/or (vii) improved implant deployment methods.

Thumb arthritis or basal joint arthritis can be caused by cartilage in the joint at the base of the thumb wearing out or being damaged. Thumb arthritis can cause debilitating hand pain, making simple tasks, such as turning door knobs, sink faucets, and other activities, difficult. Treatment has generally been limited to immobilization, pain relief medicaments, removal of the trapezium, and/or ligament reconstruction and tendon interposition (LRTI). While these treatments may reduce pain, they inhibit function of the thumb and the hand and may result in further or ongoing medicament use. Devices (e.g., implants), systems, kits, and methods described herein can provide a treatment for thumb arthritis that preserves the trapezium.

Figure 1C:
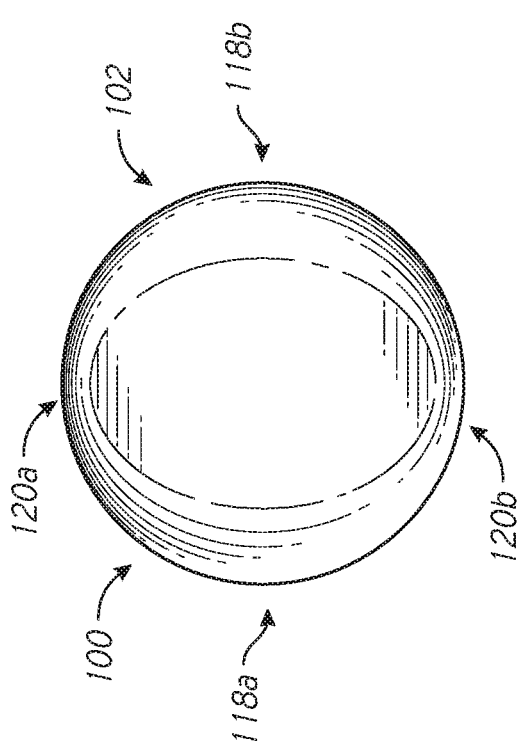
FIG. 1C is a top plan view of the implant of FIG. 1A.
Figure 1A:
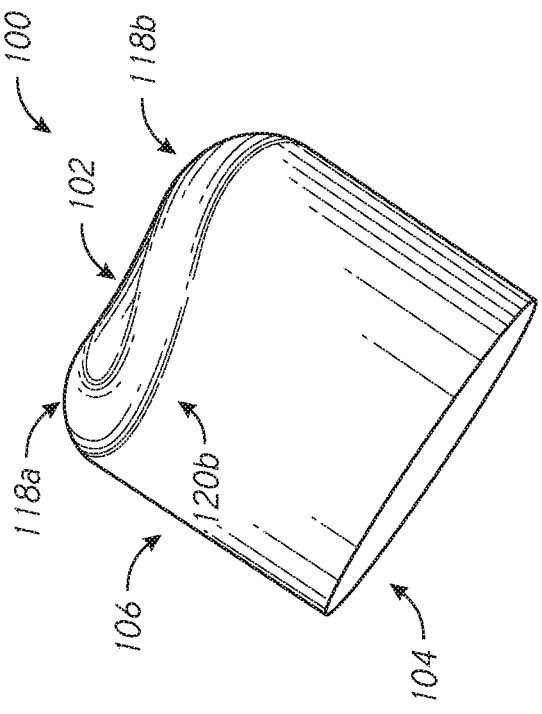
FIG. 1A is a bottom and side perspective view of an example carpometacarpal implant.

FIG. 1A is a bottom and side perspective view of one embodiment of a carpometacarpal (CMC) implant 100. FIG. 1B is a top and side perspective view of the implant 100 of FIG. 1A. FIG. 1C is a top plan view of the implant 100 of FIG. 1A. In some embodiments, the implant 100 comprises, or alternatively consists essentially of, a hydrogel, such as, for example, polyvinyl alcohol (PVA), other polymeric materials, and/or the like. In some embodiments, the PVA content of a hydrogel is about 40% by weight. The PVA content of hydrogel in an implant 100 can be less than or more than about 40% by weight (e.g., about 10%, about 15%, about 20%, about 25%, about 30%, about 32%, about 34%, about 36%, about 37%, about 38%, about 39%, about 41%, about 42%, about 43%, about 44%, about 46%, about 48%, about 50%, about 55%, about 60%, about 65%, about 70%, less than about 10%, more than about 70%, ranges between such values, etc.), as desired or required.

The hydrogel of the implant 100, as well as other implants disclosed herein, can comprise water, saline, other liquids, combinations thereof, and/or the like. In some embodiments, saline may be used instead of water, because, under certain circumstances, saline can help maintain osmotic balance with surrounding anatomical tissues following implantation. The exact composition of hydrogel in an implant 100 (e.g., PVA or other hydrogel materials, water, saline or other liquids, other additives, etc.) can be selected so as to provide the implant 100 with the desired or required strength, load bearing capacity, compressibility, flexibility, longevity, durability, resilience, coefficient of friction, and/or other properties and characteristics. In some embodiments, any hydrogel portion of the implants disclosed herein consist essentially of saline and PVA. In some embodiments, such hydrogel portions of the implants do not comprise any additional additives (e.g., growth factors, surface or other coatings, etc.). In addition, according to some embodiments, the hydrogel portions of any of the implant configurations disclosed herein comprise a consistent concentration (e.g., no concentration gradients), density, and/or other chemical and/or physical properties throughout.

In some embodiments, the implant 100, as well as other implants disclosed herein, is configured or adapted for drug delivery and/or is seeded with growth factors and/or cells. In some embodiments, the implant 100 comprises one or more of the following: chondrocytes, growth factors, bone morphogenetic proteins, collagen, hyaluronic acid, nucleic acids, and stem cells. Such factors and/or any other materials included in the implant 100 and selectively delivered to an implant site can help facilitate and/or promote the long-term fixation of the implant 100 at the joint or other target area of the anatomy.

In some embodiments, the hydrogel comprises PVA and/or any other polymeric material. In some embodiments, the content of PVA in the hydrogel is between about 35% and about 45% by weight (e.g., about 35%, about 36%, about 37%, about 38%, about 39%, about 40%, about 41%, about 42%, about 43%, about 44%, about 45%, ranges between such values, etc.). In some embodiments, the content of PVA in the hydrogel is greater than about 45% by weight (e.g., about 45%, about 50%, about 55%, about 60%, about 65%, about 70%, greater than about 70%, ranges between such values, etc.) or less than about 35% by weight (e.g., about 5%, about 10%, about 15%, about 20%, about 25%, about 30%, about 35%, ranges between such values, less than about 5%, etc.). In some embodiments, the content of PVA or other component in the hydrogel is about 40% by weight.

In some embodiments, the implant 100 is load bearing and generally non-biodegradable (e.g., non-bioerodible). In some embodiments, the implant 100 is configured or adapted for placement in at least one of a toe, finger, ankle, knee, shoulder, hip, or any other joint, preferably a carpometacarpal joint and more preferably between a first metacarpal bone and a trapezium. In some embodiments, a transition between the upper surface 102 and the sidewalls 106 is generally arcuate, curved, or otherwise smooth, for example compared to including an angle or corner. In some embodiments, such a transition can be non-curved or non-smooth, as desired or required.

In some embodiments, the implants disclosed herein are configured for anchoring during implantation. The implant can comprise one or more anchor sites (e.g., comprising non-hydrogel portions or tabs) to facilitate anchoring (e.g., suturing, stapling, etc.). In some embodiments, the implant is pre-coupled to one or more anchors. Such anchors can comprise removable and/or permanent fixtures. In some embodiments, the anchors are resorbable or otherwise dissolvable after implantation (e.g., following a particular time period, such as, for instance, 1-30 days, 2-30 weeks, 6-12 months, 1-5 years, greater than 5 years, less than 1 day, etc.). In some embodiments, the implant comprises at least one abrasive surface. In some embodiments, the implant comprises one or more adhesive components. In some embodiments, one or more implant surfaces can be configured to promote bone adhesion by one or more coatings, substances, and/or the like and/or by using an appropriate surface texture along the surface(s). For example, the implant surface can be roughened, can include pores (e.g., superficial pores), and/or can include any other feature, as desired or required.

In some embodiments, the implants disclosed herein are supported or reinforced by a rigid support frame, such as a ceramic, metallic, or other type (e.g., plastic, composite, etc.) of frame. In some embodiments, the implants disclosed herein are supported or reinforced by a flexible or rigid mesh structure. In some embodiments, the implants do not contain or are substantially free or free of any support or reinforcement structure.

Any of the implant embodiments disclosed herein, or equivalents thereof, can be manufactured using freeze/thaw cycling and/or any other production method. For example, a hydrogel formulation comprising water, saline, PVA (and/or other hydrogel materials), other polymeric materials, other additives, and/or the like can be heated and/or otherwise treated as part of a freeze/thaw manufacturing process.

In some embodiments, a hydrogel solution comprising saline and about 40% PVA by weight is heated to about 121° C. under elevated pressure conditions (e.g., to effect dissolution of the polymer). For example, such a solution can be autoclaved to facilitate complete or substantially complete dissolution of the PVA in the saline, water, and/or other liquid. Next, the temperature and/or pressure of the solution can be lowered to permit entrapped air and/or other gases to escape. In some embodiments, after the autoclaving or similar step, the solution is generally maintained at a temperature of approximately 95° C. and atmospheric pressure for a predetermined time period.

The solution can then be transferred (e.g., pumped, poured, etc.) into an open mold where, once set, the solution forms the desired shape of the implant. The mold can include a plurality of individual mold cavities, each of which is configured to receive a hydrogel solution to form an implant. The hydrogel solution may be configured to fill only a lower portion of a cavity of a mold, or the cavity can be filled with the hydrogel solution to a level above the lower portion of the cavity including an upper portion of the cavity. The cavity of the mold can be shaped, sized, and/or otherwise configured so that the implant formed therein comprises a desired configuration. Once the implant has been molded, the implant can be removed from the mold. The implant can be removed either after initial formation or after undergoing additional treatment (e.g., freeze/thaw cycling, other heat and/or pressure treatment, etc.). The implant may be cut, altered, or otherwise processed. For example, a portion of the implant formed in an upper portion of the cavity may be excised and discarded as part of a subsequent reshaping step.

Due in part to the remaining production steps, accommodation of any changes in size (e.g., expansion, contraction, etc.) that may occur or are likely to occur to the implants can be considered during manufacturing by properly sizing and otherwise designing the mold. The amount of contraction or expansion of the implant can be based on one or more factors or conditions, such as, for example, the number of freeze/thaw cycles to which the implant is subjected, the temperature and/or pressure ranges associated with the remaining steps, and/or the like.

In some embodiments, the implant can be formed, at least in part, using an injection molding process and/or any other molding or casting procedure. In such injection or transfer molding techniques, once the hydrogel or other implant solution has been prepared, the solution can be loaded into an injection cylinder or other container of a molding press. The solution can then be forcibly transferred into a closed mold assembly using a pneumatic or hydraulic ram or any other electromechanical device, system, and/or method. In some embodiments, the hydrogel and/or other solution or implant component is injected into a corresponding closed mold assembly through a standard runner and gate system. Injection molding of implants can provide one or more benefits relative to open mold assemblies. For example, an implant formed using an injection molding technique may be substantially free of or free of additional cutting, reshaping, resizing, and/or processing, due to being in essentially a final shape after completion of injection molding.

Regardless of how the implant is molded or otherwise shaped or manufactured, the implant can be subsequently subjected to one or more freeze/thaw cycles, as desired or required. In some embodiments, an implant in a mold cavity is cooled using a total of four freeze/thaw cycles in which the temperature is sequentially varied between about −20° C. and about 20° C. In some embodiments, the number of freeze/thaw cycles, the temperature fluctuation, and/or other details can be different than disclosed herein, in accordance with a specific production protocol and/or implant design.

Following freeze/thaw cycling, the implant can be at least partially removed (e.g., including fully removed) from the mold and placed in one or more saline and/or other fluid (e.g., other liquid) baths where the implant can be subjected to additional cooling and/or other treatment procedures (e.g., to further stabilize the physical properties of the implant). In some embodiments, the implant undergoes an additional eight freeze/thaw cycles while in saline. In some embodiments, such follow-up cooling procedures can be either different (e.g., more or fewer freeze/thaw cycles, different type of bath, etc.) or altogether eliminated from the production process, as desired or required.

When the cooling (e.g., freeze/thaw cycling) and/or other manufacturing processes have been completed, the implants can be inspected for any manufacturing flaws or other defects. At least some of the implants can be subjected to selective testing for physical and other characteristics, in accordance with the original design goals and/or target parameters. The implant may be cut or otherwise processed to remove any excess portions (e.g., flash). In some embodiments, one or more completed implant(s) is packaged in hermetically sealed plastic trays or other containers comprising foil or other types of lids or covering members. A volume of saline and/or other liquid can be included within such trays or other containers to provide hydration of the implant(s) during storage and/or any other steps preceding use. In some embodiments, the implant tray or other container is terminally sterilized using e-beam exposure between about 25 kilogray (kGy) and about 40 kGy.

Additional details related to implants comprising hydrogels, including methods of manufacturing and use, can be found in U.S. Pat. Nos. 5,981,826, 6,231,605, and PCT Patent Application Publication No. WO 2012/162552, each of which is hereby incorporated by reference in its entirety for all purposes.

In some embodiments, the implant 100 has a lateral dimension (e.g., diameter) between about 4 mm and about 8 mm (e.g., about 4 mm, about 5 mm, about 6 mm, about 7 mm, about 8 mm, ranges between such values, etc.), as measured in an uncompressed state. Lateral dimensions smaller than about 4 mm (e.g., between about 2 mm and about 4 mm) and larger than about 8 mm (e.g., between about 8 mm and about 10 mm) are also possible for use in subjects with small or large bones, respectively.

In some embodiments, the implant 100 comprises, or alternatively consists essentially of, or alternatively consists of, a top or upper surface 102, a bottom or lower surface 104 generally opposite the upper surface 102, and a hydrogel body between the upper surface 102 and the lower surface 104. In some embodiments, the implant 100 comprises a hydrogel (e.g., PVA) implant 100 or any other type of substrate-based implant 100. In some embodiments, the implant 100 is capable of being used and/or is configured to be used in a joint treatment method as disclosed herein, modifications thereof, and/or other methods. In some embodiments, sidewalls 106 generally extend between the upper surface 102 and the lower surface 104. In some embodiments, the implant 100 is configured for placement in an implant site having a corresponding recess.

In some embodiments, the overall height (e.g., between the top surface 102 and the bottom surface 104) of the implant 100 is between about 4 mm and about 8 mm (e.g., about 4 mm, about 5 mm, about 6 mm, about 7 mm, about 8 mm, ranges between such values, etc.), as measured in an uncompressed state. Heights smaller than about 4 mm (e.g., between about 2 mm and about 4 mm) and larger than about 8 mm (e.g., between about 8 mm and about 10 mm) are also possible for use in subjects with small or large bones, respectively.

The upper surface 102 may be configured to form an articulation surface when the implant 100 is implanted in a joint. As shown, the upper surface 102 can comprise a contour configured to correspond to contours of a lower surface of a first metacarpal bone (facing the trapezium) and/or an upper surface of a trapezium (facing the first metacarpal bone). In some embodiments, the upper surface 102 has a saddle shape comprising peaks 118a, 118b and troughs 120a, 120b. The contours of the upper surface 102 are illustrated by line contours in FIG. 1C. The contours of the upper surface 102 of the implant 100 may be modified to match a specific anatomy (e.g., a surface (e.g., inferior surface) of a trapezium). In some embodiments, a surface of a bone (e.g., first metacarpal bone) and/or an opposing bone (e.g., trapezium) may be scanned (e.g., via computerized tomography (CT), computerized axial tomography (CAT), positron emission tomography (PET), magnetic resonance imaging (MRI), combinations thereof, etc.), which can be used to make a mold (e.g., via 3D printing, CAD-CAM milling, etc.) to match specific anatomical features of a specific patient or subject, which can be advantageous, for example, when the anatomy has been damaged or otherwise includes unique characteristics.

The upper surface 102 comprises, or alternatively consists essentially of, or alternatively consists of, a saddle shape including a first peak 118a, a second peak 118b, a first trough 120a laterally between the first peak 118a and the second peak 118b, and a second trough 120b laterally between the first peak 118a and the second peak 118b. The first peak 118a is laterally between the first trough 120a and the second trough 120b. The second peak 118b is laterally between the first trough 120a and the second trough 120b. In some embodiments, a distance between the first peak 118a and/or the second peak 118b and the lower surface 104 is between about 10% and about 20% greater than a distance between at least one of the first trough 120a and the second trough 120b and the lower surface 104. One or both of the peaks 118a, 118b may be between about 1 mm and about 1.5 mm (e.g., about 1 mm, about 1.1 mm, about 1.2 mm, about 1.3 mm, about 1.4 mm, about 1.5 mm, ranges between such values, etc.) higher than one or both of the troughs 120a, 120b.

Although the implant 100 is illustrated as a substantially cylindrical plug or shape, other shapes of the implant 100 are also possible. For example, an upper surface 102 and/or the lower surface 104 may be contoured to abut particular anatomy (e.g., planar (e.g., flat), non-planar (e.g., curved, concave, convex, undulating, fluted)) and/or modified anatomy (e.g., a recess formed in a bone). The implant 100 can include a generally circular or oval cross-sectional shape. In some embodiments, the implant 100 is generally shaped like a cylinder. The overall shape of any of the implants disclosed herein can vary depending on the specific application or use. For example, the shape of at least part of the implant 100 can be generally polygonal (e.g., rectangular, round, hexagonal), irregular, and/or the like.

In some embodiments, the implant 100 lacks, is devoid of, is substantially free of, etc. attachment tabs or other features configured to fix the implant 100 in place. For example, the implant 100 may maintain position by being slightly oversized with respect to a cavity in which a portion of the implant 100 is positioned.

In some embodiments, the implant 100 lacks, is devoid of, is substantially free of, etc. surface contours on the bottom surface 104. For example, the implant 100 may lack configuration to be placed between a first metacarpal bone and a trapezium without forming a cavity in the first metacarpal bone.

In some embodiments, the implant 100 lacks, is devoid of, is substantially free of, etc. an upper surface 102 configured to replace a bone or an end of a bone. For example, the implant 100 may be configured to replace part of an end surface of a bone (e.g., a central portion, a bearing surface, etc.), but not to replace the entire bone and/or the end surface.

FIGS. 2A-5B illustrate example tooling or systems that may be used to deploy the implant 100 in a carpometacarpal joint such as between the first metacarpal bone and the trapezium. The implant 100 or variations thereof may also be used at other joints. In some embodiments, a plurality of implants (e.g., the implant 100) may be used in a carpometacarpal joint or other joints. In certain instances, reference is made to FIGS. 6A-6Z to illustrate or explain an aspect, potential advantage, etc. of a tool or system. One or more of the tools can be used in combination with a substantially cylindrical, elongate guide pin having a sharpened end (or another guiding device), which can aid in alignment of the tools throughout a treatment method. In some embodiments in which an implant comprises a bone anchor, the bone anchor may fit in a hole created by the guide pin. Absence of a guide pin or other guiding device is also possible.

FIGS. 2A-3D illustrate example components of a system, for example, usable to create a cavity into which the implant 100 may be inserted. The introducer placer 200 of FIGS. 2A-2C may be used in combination with a drill bit or other system different than the drill bit 300 of FIGS. 3A-3D. The drill bit 300 of FIGS. 3A-3D may be used in combination with a placer or other system different than the placer 200 of FIGS. 2A-2C. Other systems and methods for creating a cavity are also possible, including modifications to the placer 200 and/or the drill bit 300. The spacer 200 and/or drill bit 300 may be used in combination with the introducer 400 of FIGS. 4A and 4B, other introducers, the plunger 500 of FIGS. 5A and 5B, other plungers, or other systems.

FIG. 2A is a side perspective view of an example placer 200. The placer 200 comprises a first end 202, a second end 204 generally opposite the first end 202, and a body 206 extending between the first end 202 and the second end 204. The body 206 is generally cylindrical, although other shapes are also possible (e.g., having an elliptical cross-section, having a polygonal cross-section, etc.). The placer 200 can comprise stainless steel (e.g., surgical grade stainless steel), plastic, combinations thereof, and/or the like.

FIG. 2B is a first end 202 and side perspective view of the placer 200 of FIG. 2A. In some embodiments, the first end 202 has a saddle shape comprising peaks 218a, 218b and troughs 220a, 220b. The contours of the first end 202 are illustrated by line contours in FIG. 2B. The contours of the first end 202 may be modified to match a specific anatomy (e.g., a surface (e.g., inferior surface) of a trapezium) and/or anatomy of a specific patient or subject (e.g., using scanning and manufacturing process as described herein). In certain such embodiments, the first end 202 of the placer 200 may be exchangeable (e.g., using a first end 202 configured to engage a standard body 206 using threads or other attachment mechanism). In some embodiments, the first end 202 is substantially flat or planar.

FIG. 2C is a second end 204 and side perspective view of the placer 200 of FIG. 2A. In some embodiments, the second end 204 is substantially flat or planar. In some embodiments, the second end 204 has a shape configured to correspond to a shape created by a certain drill bit. In certain such embodiments, the second end 204 of the placer 200 may be exchangeable (e.g., using a second end 204 configured to engage a standard body 206 using threads or other attachment mechanism). The body 206 may comprise a substantially cylindrical body having threads or other coupling mechanisms at one or both ends for coupling to a modular first end 202 (e.g., for different anatomies) and/or a modular second end 204 (e.g., for different drill bits). The threads or other coupling mechanisms at one or both ends may be the same (e.g., to allow either side of the body 206 to be used for the first end 202 or the second end 204) or different (e.g., to inhibit or prevent use of different sides of the body 206 for the same ends 202, 204).

In some embodiments, the placer 200 includes a lumen 208 in the body 206 between the first end 202 and the second end 204. The lumen 208 is configured to accept a guide pin therethrough, for example as described with respect to FIG. 6E. The lumen 208 may be centered in the body 206 or may be radially offset. In some embodiments, the body 206 comprises a plurality of lumens (e.g., allowing a user to select a lumen based on the interaction of the first end 202 of the spacer 200 with the anatomy). In some embodiments, the drill bit 300 can be advanced to the targeted drill site of the patient bone or other anatomical location with the assistance of a guide pin or other guiding device or member. A cannulated drill bit 300, as discussed herein, can be passed over the guide pin to ensure that the distal, working end 302 of the drill bit 300 is properly positioned relative to the treatment site (e.g., bone, joint).

The placer 200 may comprise, for example proximate to the second end 204, a plurality of arcuate bands 210a, 210b, 210c, 210d, 210e that can be used to measure depth of a cavity, for example a cavity resulting from drilling into bone. In some embodiments, the band 210a may correspond to a depth from the second end 204 of about 6 mm, the band 210a may correspond to a depth from the second end 204 of about 6 mm, the band 210b may correspond to a depth from the second end 204 of about 7 mm, the band 210c may correspond to a depth from the second end 204 of about 8 mm, the band 210d may correspond to a depth from the second end 204 of about 9 mm, and the band 210e may correspond to a depth from the second end 204 of about 10 mm, the bands 210a, 210b, 210c, 210d, 210e being spaced by about 1 mm. The bands 210a, 210b, 210c, 210d, 210e may be spaced by about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, greater than about 2 mm, combinations thereof, and the like. The plurality of bands may comprise between four bands and six bands (e.g., four, five, six, ranges between such values, etc.). More bands (e.g., between six bands and ten bands) or fewer bands (e.g., between one band and four bands) are also possible. For example, the bands may start closer to the second end 204 (e.g., about 0.1 mm, about 0.5 mm, about 1 mm, etc. from the second end 204). The bands may be fully arcuate (e.g., extending around part of the circumference of the body 206) and/or partially arcuate (e.g., extending around part of the circumference of the body 206). The bands may each be the same or may be different from each other. The bands may be used to measure a depth of a drilled hole in a bone, for example as described in further detail with respect to FIG. 6K. In some embodiments, the bands may comprise distinguishing indicia. For example, the bands may comprise different dash patterns (e.g., a dotted band 210a, a solid band 210b, a dashed band 210c, a solid band 210d, and a dotted band 210e), different colors (e.g., different colors in the color palette, different shades, etc.), numbers (e.g., indicative of depth, band number, etc.), combinations thereof, and the like.

The placer 200 may comprise the features described herein with respect to one or both of the first end 202 (e.g., a saddle shape) and the second end 204 (e.g., measurement bands). In some embodiments, a first tool can include the features of the first end 202 and a second, separate, tool can include the features of the second end 204.

FIG. 3A is a side and bottom perspective view of an example drill bit 300. FIG. 3B is a side perspective view of the drill bit 300 of FIG. 3A. FIG. 3C is a bottom plan view of the drill bit 300 of FIG. 3A. FIG. 3D is a top and side perspective view of the drill bit 300 of FIG. 3A. The drill bit 300 can be used to create a recess or hole or cavity or aperture or crater or pit or pocket in a bone, for example in which an implant 100 can be placed. The drill bit 300 comprises, or alternatively consists essentially of, a distal end 302, a proximal end 304 generally opposite the distal end 302, and a body 306 extending between the distal end 302 and the proximal end 304. The drill bit 300 may comprise, for example, stainless steel.

In some embodiments, the body 306 of the drill bit 300 includes a generally cylindrical distal section 306a and a polygonal proximal section 306b. The cylindrical distal section 306a may provide strength to the drill bit 300 and/or reduce eccentricity during drill rotation. The polygonal proximal section 306b is sized, shaped, and otherwise configured to selectively mate with a corresponding portion of a bone drill (not shown). In some arrangements, the proximal section 306b comprises a generally triangular cross-sectional area, but other shapes, sizes, and/or other details of the proximal section 306b can vary. Other shapes of the body 306, including the distal section 306a and/or the proximal section 306b, are also possible. Bone drills with which the drill bit 300 or variations thereof can be coupled may be manually operated and/or power driven (e.g., mechanically, pneumatically, hydraulically, etc.).

The distal end 302 of the drill bit 300 can include a flange 312 and one or more abrading members or blades or cutters 310a, 310b, 310c extending distally from the flange 312. As best illustrated in FIG. 3C, the drill bit 300 can comprise a total of three cutters 310a, 310b, 310c that are generally equally spaced apart (e.g., at angles of approximately 120° relative to each other). The quantity, size, shape, position, orientation, spacing, and/or other characteristics or properties of the cutters 310 can vary. For example, a drill bit can include more than three cutters or fewer than three cutters (e.g., 1, 2, 4, 5, more than 5, etc.), as desired or required. For another example, a drill bit can include cutters that are larger and/or smaller, that extend along different portions of the distal end of the drill bit, combinations thereof, and the like. The flange 312 can provide a non-cutting "stop" surface that can inhibit the drill bit 300 from cutting below a certain depth, even if further rotation and pressure are applied. The flange 312 can aid in removal of cut material, for example inhibiting or preventing cut material from spraying past the flange unabated.

In some embodiments, the drill bit 300 comprises a lumen 308 extending (e.g., longitudinally) through the drill bit 300. For example, as illustrated in FIGS. 3A and 3D, the lumen 308 can generally extend from the distal end 302 to the proximal end 304. As described herein, a lumen 308 can help ensure that the drill bit 300 is accurately positioned relative to a joint, bone, and/or other portion of anatomy of a subject (e.g., over a guide pin) before commencing and/or during a drilling procedure.

As the drill bit 300 is rotated (e.g., either manually or using one or more external driving sources, etc.), sharp edges formed along the distal and/or peripheral portions of the cutters 310a, 310b, 310c can abrade and remove cartilage, bone, and/or other tissue. In some embodiments, the longitudinal distance between the distal face of the flange 312 and the distal ends of the cutters 310a, 310b, 310c can limit the depth of the recess or opening that is created by the drill bit 300. Peripheral surfaces of the cutters 310a, 310b, 310c can define a diameter $\varphi_c$ (FIG. 3C) or other cross-sectional dimension that can limit the diameter of the resulting recess or other openings that is created by the drill bit 300. Peripheral surfaces of the flange 312 can define a diameter $\varphi_f$ (FIG. 3C) greater than $\varphi_c$ or other cross-sectional dimension that can limit the depth of the resulting recess or other openings that is created by the drill bit 300. The drill bit 300 can thereby be configured to create an implant site having specific dimensions (e.g., depth, diameter, etc.). In some embodiments, drill bits of varying size and shape are available to the surgeon or other clinician in order to accurately create a specific desired implant site. For any of the embodiments disclosed herein, the distal edges and/or other surfaces of the cutting blades or cutters can be generally flat and/or otherwise contoured (e.g., to generally match and/or receive the base of the implant).

As the drill bit 300 is rotated and advanced into a targeted region of the patient's anatomy, abraded bone, cartilage and/or other tissue, and/or other debris is created at or near the distal end 302. To permit such debris to be removed from the treatment site, the flange 312 can include one or more openings, for example in the form of through holes, channels, edge features, etc. Abraded materials can stay clear of and not interfere with the working end of the drill bit 300, allowing the cutters 310a, 310b, 310c to continue to function normally. Once the distal face of the flange 312 abuts the top surface of the bone being drilled, further advancement of the drill bit 300 can be inhibited or prevented. Resistance to further advancement can alert the clinician that an implant site having the desired depth and diameter has been properly created.

The cutters 310a, 310b, 310c can be joined along a hub 314 along or near the center of the distal face of the flange 312. As shown, the cutters 310a, 310b, 310c can extend at least radially outwardly from the hub 314, toward the outer periphery of the flange 312. The radial length of the cutters 310a, 310b, 310c can help determine a diameter of a recess or opening created by the drill bit 300. In embodiments in which peripheral edges of the cutters 310*a*, 310*b*, 310*c* are generally vertically oriented (e.g., as illustrated in FIG. 3B), the corresponding opening created by the drill bit 300 is generally cylindrical. In some embodiments, the cutters can extend distally from a distal-facing surface, such as the distal-facing surface of the flange 312, without a hub 314.

FIGS. 4A-5B illustrate example components of a deployment system or delivery device, for example usable to deploy the implant 100. The introducer 400 of FIGS. 4A and 4B may be used in combination with a plunger or other system different than the plunger 500 of FIGS. 5A and 5B. The plunger 500 of FIGS. 5A and 5B may be used in combination with an introducer or other system different than the introducer 400 of FIGS. 4A and 4B. Other systems and methods for deploying or delivering an implant are also possible, including modifications to the introducer 400 and/or the plunger 500. The introducer 400 and/or plunger 500 may be used in combination with the placer 200 of FIGS. 2A-2C, other placers, the drill bit 300 of FIGS. 3A-3D, other placers, or other systems.

FIG. 4A is a side and bottom perspective view of one embodiment of an introducer 400. The introducer 400 can comprise, or alternatively consist essentially of, a distal end 402, a proximal end 404 generally opposite the distal end 402, and a generally cylindrical tube 406 having an opening or lumen 408 through which an implant (e.g., the implant 100) may be passed. In some embodiments, the distal end 402 of the introducer 400 comprises a neck portion or other narrowed portion 410. The neck portion 410 is configured to be positioned at least partially in a recess created by a drill bit and in which an implant will be at least partially secured. In some embodiments, the introducer 400 is sized, shaped, and otherwise configured to that the neck portion 410 fits generally snugly within the implant site. The shoulder 412 or other feature where the introducer 400 returns to the normal or nominal or larger diameter can act as a depth stop, which can ensure that the implant is positioned in the recess. In some embodiments, the shoulder 412 can help protect the structural integrity of the implant as the implant is being deployed. In some embodiments, the shoulder 412 comprises a distally-facing surface that is substantially flat or planar (e.g., as illustrated in FIG. 4A). In some embodiments, the shoulder 412 comprises a distally-facing surface that is contoured (e.g., to correspond to an undrilled surface of a first metacarpal bone). The body 406 may comprise a substantially cylindrical body having threads or other coupling mechanisms for coupling to a modular distal end 402 (e.g., for different anatomies).

FIG. 4B is a side and top perspective view of the introducer 400 of FIG. 4A. The internal diameter of the introducer 400 can vary along its longitudinal length. For example, as shown in FIG. 4B, the proximal end 404 of the introducer 400 comprises, at least partially, a flared shape 414 in which at least a portion of the inside diameter of the lumen 408 is progressively reduced in the proximal to distal direction. The lumen 408 can maintain a generally constant inner diameter distal to the flared shape 414 forming a generally cylindrical interior portion. The lumen 408 can have a diameter that his smaller than a diameter of an uncompressed implant such that the implant is radially inwardly compressed as the implant is distally advanced through the flared shape 414. In some embodiments, compression of the implant may aid in deployment of the implant by allowing the compressed implant to be positioned in a recess in bone having a smaller diameter than a diameter of the uncompressed implant, which can allow the implant to radially outwardly expand to provide apposition against sidewalls of the recess. In some embodiments, compression of the implant may inhibit the implant from falling out of the introducer 400 during deployment (e.g., due to apposition of the implant against sidewalls of the lumen 408).

In some embodiments, the introducer 400 comprises alignment indicia 416 configured to align an implant having a contoured surface (e.g., a contoured upper surface) before and/or during deployment. As described with respect to FIGS. 6O-6T, the trough 120*a* or 120*b* of an implant 100 having a saddle shape may be aligned with the indicia 416 at the proximal end 404 of the introducer 400. The indicia 416 may include pictures or other terms indicative of what should be aligned (e.g., a trough shape as shown in FIG. 4A, the term "trough," combinations thereof, and the like). As described with respect to FIGS. 6U-6X, the trough 20*a* or 20*b* of a bone surface having a saddle shape may be aligned with the indicia 416 at the distal end 402 of the introducer 400. In some embodiments, compression of the implant can inhibit or prevent rotation of the implant in the introducer 400 such that alignment at the proximal end 404 can provide alignment at the distal end 402. In some embodiments, the peak 118*a* or 118*b* of an implant 100 having a saddle shape may be aligned with the indicia 416. In some embodiments in which the implant has a non-circular lateral cross-section (e.g., elliptical, polygonal, etc.), the lumen 408 may have a corresponding lateral cross-section, which can inhibit or prevent rotation of the implant in the introducer 400 such that alignment at the proximal end 404 can provide alignment at the distal end 402.

In some embodiments, the introducer 400 comprises a viewing window that permits an implant to be viewed as it is advanced through the introducer 400, for example prior to and/or during deployment. The viewing window can be separate or integrated as part of the alignment indicia 416. For example, the alignment indicia 416 may comprise ink, etching, and/or windows (e.g., comprising unfilled slits and/or a biologically compatible non-opaque or at least partially optically transparent material).

In some embodiments, the inner diameter, length, other dimension, and/or other details or properties of the introducer 400, including a flared shape 414, a generally cylindrical interior portion, a neck portion 410, and/or the like can be different than shown and described herein. For example, the flared shape 414 can extend along more, or even all or substantially all, of the length of the lumen 408. For another example, the interior surface of the body 406 may be at least partially non-linear (e.g., curved, rounded, irregular, etc.), in addition to or in lieu of any generally linear and/or constant portions, as desired or required.

In some embodiments, the longitudinal axis of the introducer 400 (and the longitudinal axis along which the implant is advanced through the introducer 400) is substantially perpendicular or perpendicular with or at another desired angle to the surface of the bone or other anatomical site (e.g., bottom of the recess) into which the implant will be delivered and/or the distal end 402 or a portion thereof is substantially parallel or parallel to a longitudinal axis of the bone or other anatomical structure (e.g., longitudinal axis of the recess).

In some embodiments, at least a portion of the interior of the introducer 400 comprises and/or is coated or lined with one or more absorbable or lubricious layers, materials, and/or other substances. Such materials can help preserve a moisture level of the implant during deployment. The interior surface of the introducer 400 can comprise a low coefficient of friction to facilitate the delivery of an implant through the lumen 408. In some embodiments, reducing an effective coefficient of friction along the interior of the introducer 400 can comprise polishing the interior surfaces of the introducer 400. The introducer 400, including interior surfaces, can comprise stainless steel (e.g., surgical grade stainless steel), titanium, other metals and/or alloys, plastic, combinations thereof, and/or the like.

FIG. 5A is a side and bottom perspective view of an example plunger 500. FIG. 5B is a side perspective view of the plunger 500 of FIG. 5A. The plunger 500 may be used in combination with the introducer 400 to form a deployment system. The plunger 500 comprises, or alternatively consists essentially of, a distal end 502, a proximal end 504 generally opposite the distal end 502, and a body 506 between the distal end 502 and the proximal end 504.

The distal end 502 has a saddle shape comprising peaks 518*a*, 518*b* and troughs 520*a*, 520*b*. The contours of the distal end 502 are of the plunger 500 may be modified to match a specific anatomy (e.g., a surface (e.g., inferior surface) of a trapezium). The body 506 may comprise a substantially cylindrical body having threads or other coupling mechanisms for coupling to a modular distal end 502 (e.g., for different anatomies). In some embodiments, a modular distal end can be used as the distal end 202 of the spacer 200 and the distal end 502 of the plunger 500. As described with respect to FIGS. 6Q-6T, the peaks 118*a*, 118*b* and troughs 120*a*, 120*b* of an implant 100 having a saddle shape may be aligned with the peaks 518*a*, 518*b* and troughs 520*a*, 520*b* of the distal end 502 of the plunger 500. Although the fit of the implant in the introducer 400 may inhibit or prevent rotation, a properly seated plunger 500 (e.g., with the contours of the distal end 502 aligned with the contours of an implant) can be used to check for rotation. For example, as described with respect to FIG. 6V, the plunger proximal end 504 of the plunger may comprise indicia 516. The indicia 516 may include pictures or other terms indicative of what should be aligned (e.g., a trough shape as shown in FIGS. 5A and 5B, the term "trough," combinations thereof, and the like). In some embodiments, if the indicia 516 are aligned with the indicia 416 at the proximal end 404 of the introducer 400 (e.g., as shown in FIG. 6T) and the plunger 500 is properly seated, then the implant can be expected to be aligned with the indicia 416 of the introducer 400. If the introducer 400 is properly seated (e.g., with the indicia 416 aligned with the peaks and/or troughs of a bone), then the implant should be properly aligned upon deployment. In some embodiments, the proximal end 504 (e.g., the radially outward extending arms of a T-shape) may be used as indicia 516.

The proximal end 504 of the plunger 500 may comprise an enlarged head portion 512. In some embodiments, the head portion 512 is in a T-shape (e.g., as illustrated in FIGS. 5A and 5B). In some embodiments, the head portion 512 comprises a ball, a flat surface, a handle, a grasping portion configured to be selectively gripped and manipulated, or any other surface suitable for engagement by a hand. In some embodiments, the head portion 512 is configured to engage an external power-assist device (e.g., mechanically, pneumatically, hydraulically, etc.), as desired or required. The body 506 may comprise a substantially cylindrical body having threads or other coupling mechanisms for coupling to a modular proximal end 504 (e.g., for user preference of a manual handle, for optional connection to a power-assist device).

In some embodiments, the body 506 may be the same as the body 206, and modular first or distal ends 202, 502 and/or second or proximal ends 204, 504 may be coupled for use as a spacer or a head portion. For example, a body can be coupled to a modular distal end and first modular proximal end for use as a spacer, after which the first modular proximal end can be exchanged with a second modular proximal end for use as a plunger. The bands for a spacer and the indicia for a plunger may be integrated with each other on the body, the bands may be part of a modular proximal end, and/or the indicia may be part of a modular distal end. Such embodiments can reduce costs (e.g., because the same body is used for the spacer and the plunger and/or provide better alignment (e.g., because the same modular distal end is used to guide the drill bit and to deploy the implant). If the modular distal end of the plunger does not correspond to the proximal end of the implant, that could indicate a problem with the modular distal end and/or the implant, which could inhibit or prevent placement of improper implants that may be difficult to remove once deployed.

In some embodiments, the plunger 500 includes a motion limiter or depth stop. The motion limiter can comprise one or more knobs, protrusion members, and/or other features that generally extend outwardly from the body 506 and/or the head portion 512. In some embodiments, a motion limiter is configured to slide in a portion of the lumen 408 of the introducer 400 (e.g., in the flared shape 414 but not distal thereto). A motion limiter can help inhibit or prevent distal movement of the plunger 500 relative to the introducer 400 (e.g., when the motion limiter contacts or abuts a surface of the introducer 400). A motion limited can help inhibit or prevent rotation of the plunger 500 relative to the introducer 400 during use, which can aid in proper alignment and positioning of the implant during deployment.

The body 506 of the plunger 500 can comprise a generally cylindrical shape configured to fit through the lumen 408 of the introducer 400 (e.g., including distal to the flared shape 414). The body 506 can have a lateral dimension (e.g., diameter) that is slightly smaller than a smallest lateral dimension (e.g., diameter) of the lumen 408 of the introducer 400. As discussed in greater detail herein, by actuating the deployment device, a clinician, surgeon, or other user can selectively move the plunger 500 within an interior portion of the introducer 400 in order to urge an implant (e.g., the implant 100) through the distal end 402 of the introducer 400 and in a targeted implant site. Other shapes of the body 506 are also possible (e.g., having an elliptical cross-section, having a polygonal cross-section, etc.). The body 506 may be hollow (e.g., to reduce weight or material used, if the same as the body 206), solid (e.g., to increase strength or rigidity), and the like.

In some embodiments, the deployment system or delivery device comprises and/or is operatively coupled to one or more pressure gauges or other pressure or force measuring devices, members, and/or features. Such gauges or other measurement devices can help ensure that a certain (e.g., maximum or threshold) backpressure or force is not exceeded when operating the device, which can help protect the integrity of an implant being deployed (e.g., to maintain the structural integrity, water composition, and/or other properties of the implant), protect the delivery device, protect the user and/or the subject, and/or provide one or more other advantages or benefits.

The components of the delivery device can comprise one or more rigid and/or semi-rigid materials configured to withstand the forces, moments, chemicals, and/or other substances, temperature fluctuations, and/or other elements to which they may be exposed. For example, the components of the implant delivery device can comprise one or more metals (e.g., stainless steel, surgical stainless steel, other types of steel, etc.), alloys, plastics, combinations thereof, and/or the like. Such materials can permit the device to be autoclaved, sterilized, or otherwise cleaned during a specific disinfection protocol. The structural and other physical characteristics of the device can permit the user to exert appropriate forces to deliver implants of various sizes, shapes, and/or configurations through the introducer and in a target implant site of a subject.

In some embodiments, a kit comprises at least two of the placer, drill bit, introducer, plunger, and guide pin. For example, the kit may comprise the placer and drill bit; the placer and introducer; the placer and plunger; the placer and guide pin; the placer, drill bit, and introducer; the placer, drill bit, and plunger; the placer, drill bit, and guide pin; the placer, drill bit, introducer, and plunger; the placer, drill bit, introducer, and guide pin; the placer, drill bit, plunger, and guide pin; the drill bit and introducer; the drill bit and plunger; the drill bit and guide pin; the drill bit, introducer, and plunger; the drill bit, introducer, and guide pin; the drill bit, plunger, and guide pin; the drill bit, introducer, plunger, and guide pin; the introducer and plunger; the introducer and guide pin; the introducer, plunger, and guide pin; the plunger and guide pin; the placer, drill bit, introducer, plunger, and guide pin; and any other permutations of tools described herein, modifications thereof, and the like. In certain such embodiments, the kit may comprise the implant or a plurality of implants (e.g., having different dimensions). The kit may comprise a packaging in which the components are sterilized.

In some embodiments, the kit comprises at least two of means for placing an implant (e.g., the placer), means for forming a cavity (e.g., the drill bit), and means for deploying an implant (e.g., comprising the introducer and/or the plunger). In some embodiments, the kit further comprises means for treating a joint (e.g., the implant).

In some embodiments, the kit comprises a body having a proximal end and a distal end. The distal end of the body comprises a coupling feature (e.g., threads). The kit further comprises at least one modular distal end comprising a coupling feature (e.g., threads) complementary to the coupling feature of the distal end of the body. In some embodiments, a distal surface of the modular distal end comprises a saddle shape configured to correspond to a surface of an implant. The proximal end of the body comprises a coupling feature (e.g., threads). The kit further comprises at least one modular proximal end comprising a coupling feature (e.g., threads) complementary to the coupling feature of the proximal end of the body. In some embodiments, the kit comprises a plurality of modular proximal ends. For example, a first modular proximal end may comprise a substantially flat surface and depth bands and a second modular proximal end may comprise a T-shaped handle and implant alignment indicia.

Figure 6A:
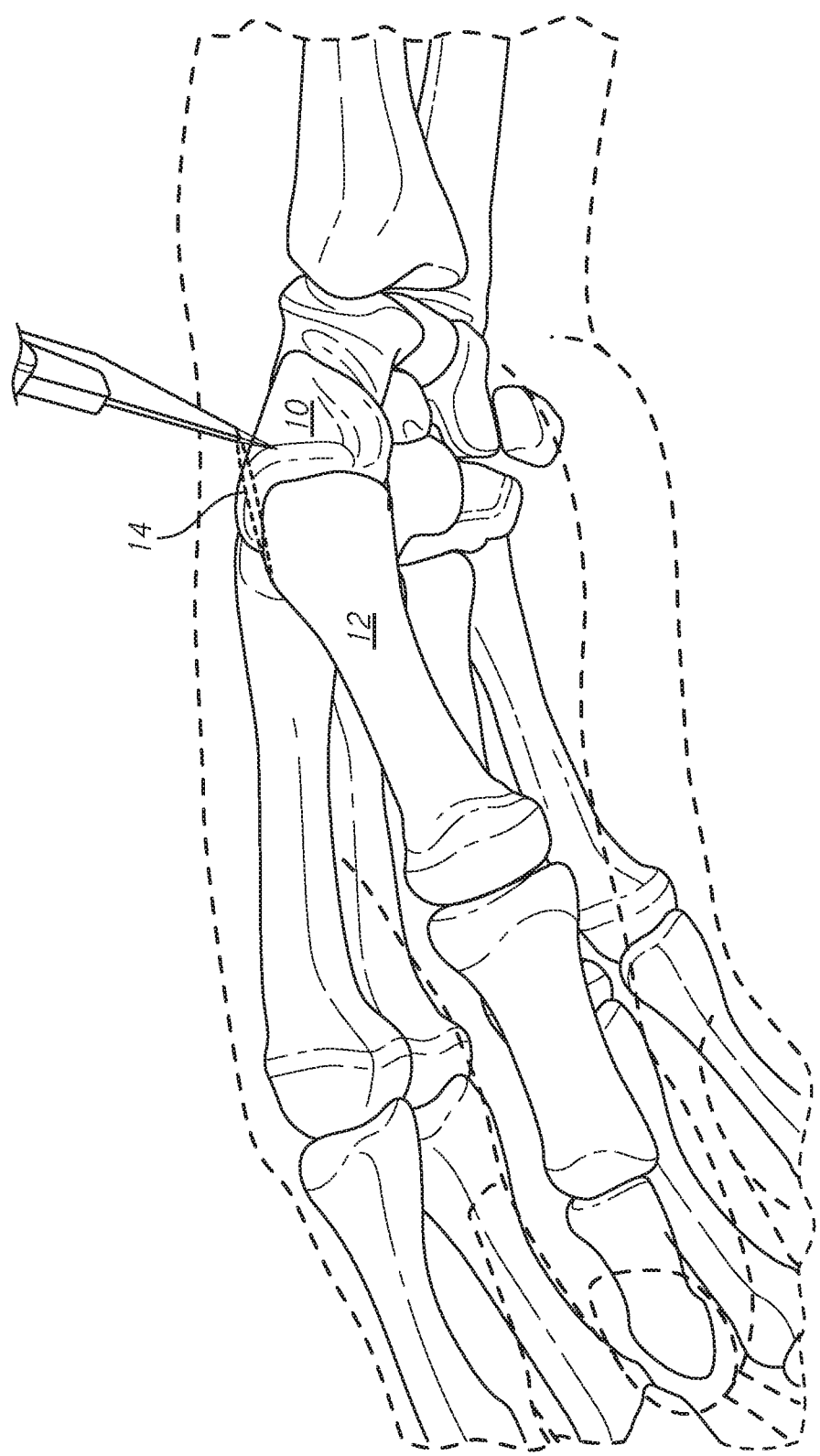
FIGS. 6A-6Z schematically illustrate an example method of positioning an example carpometacarpal implant.
Figure 6B:
Figure 6E:
Figure 6F:
Figure 6G:
Figure 6H:
Figure 61:
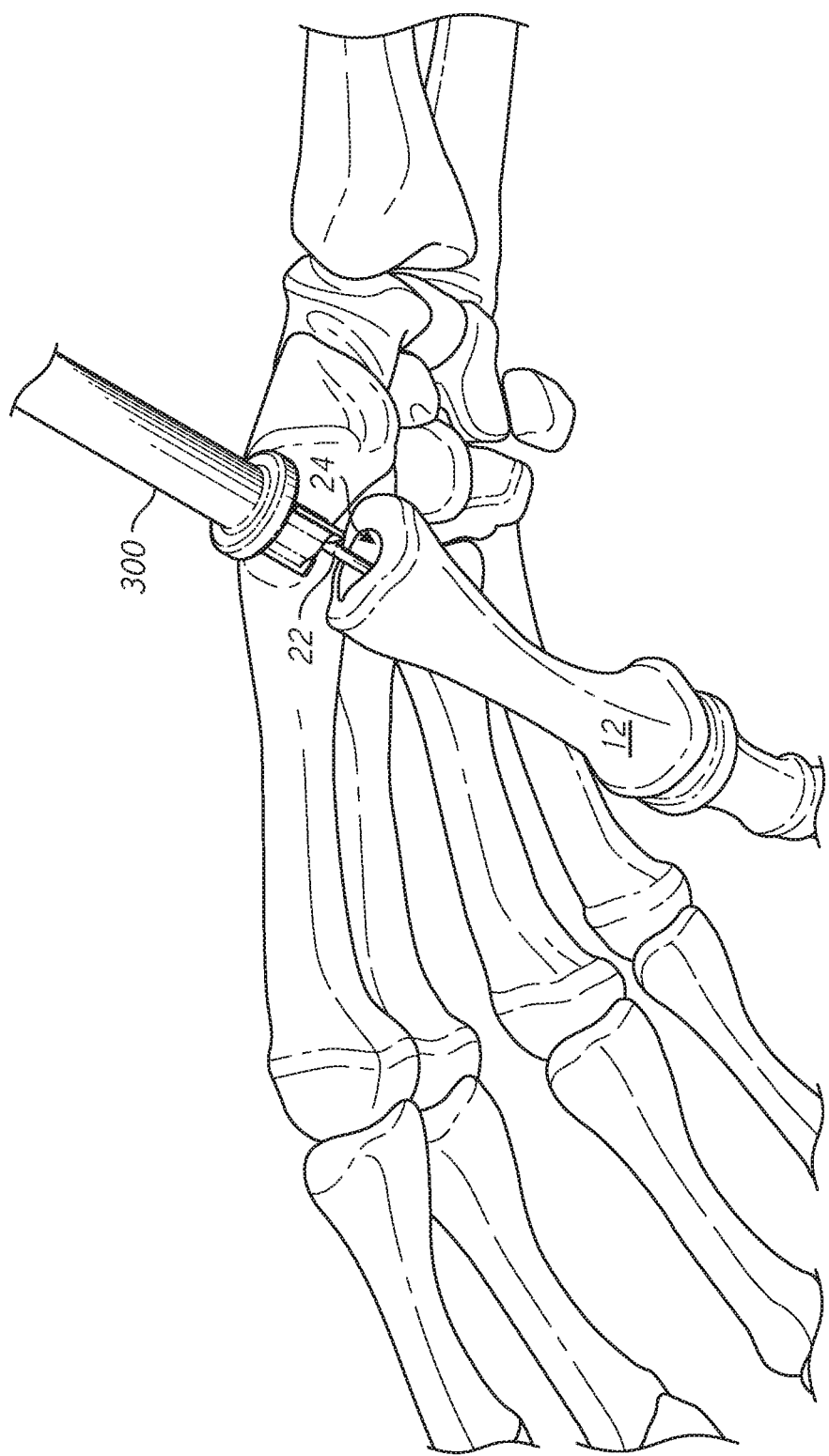
Figure 6J:
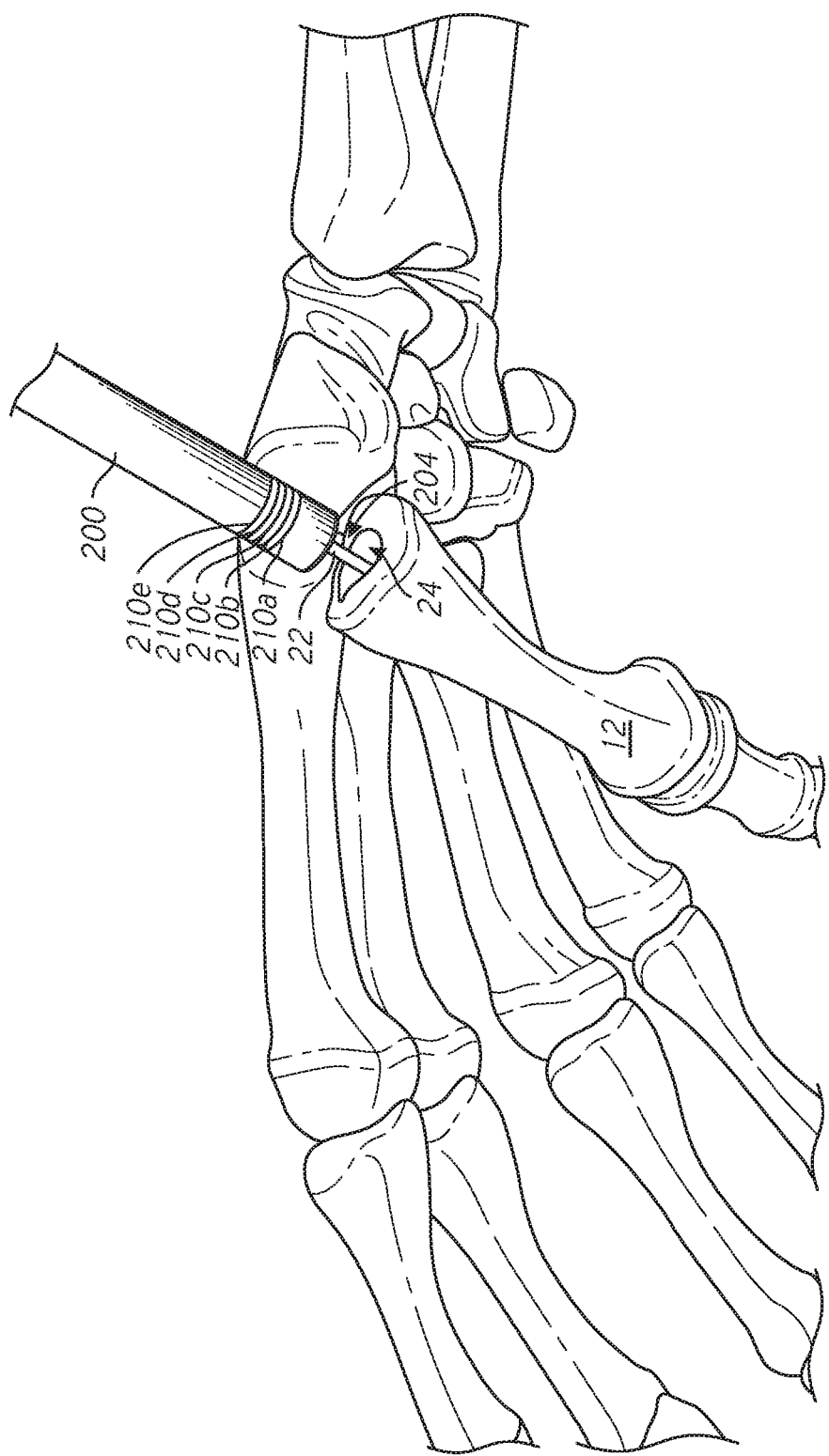
Figure 6K:
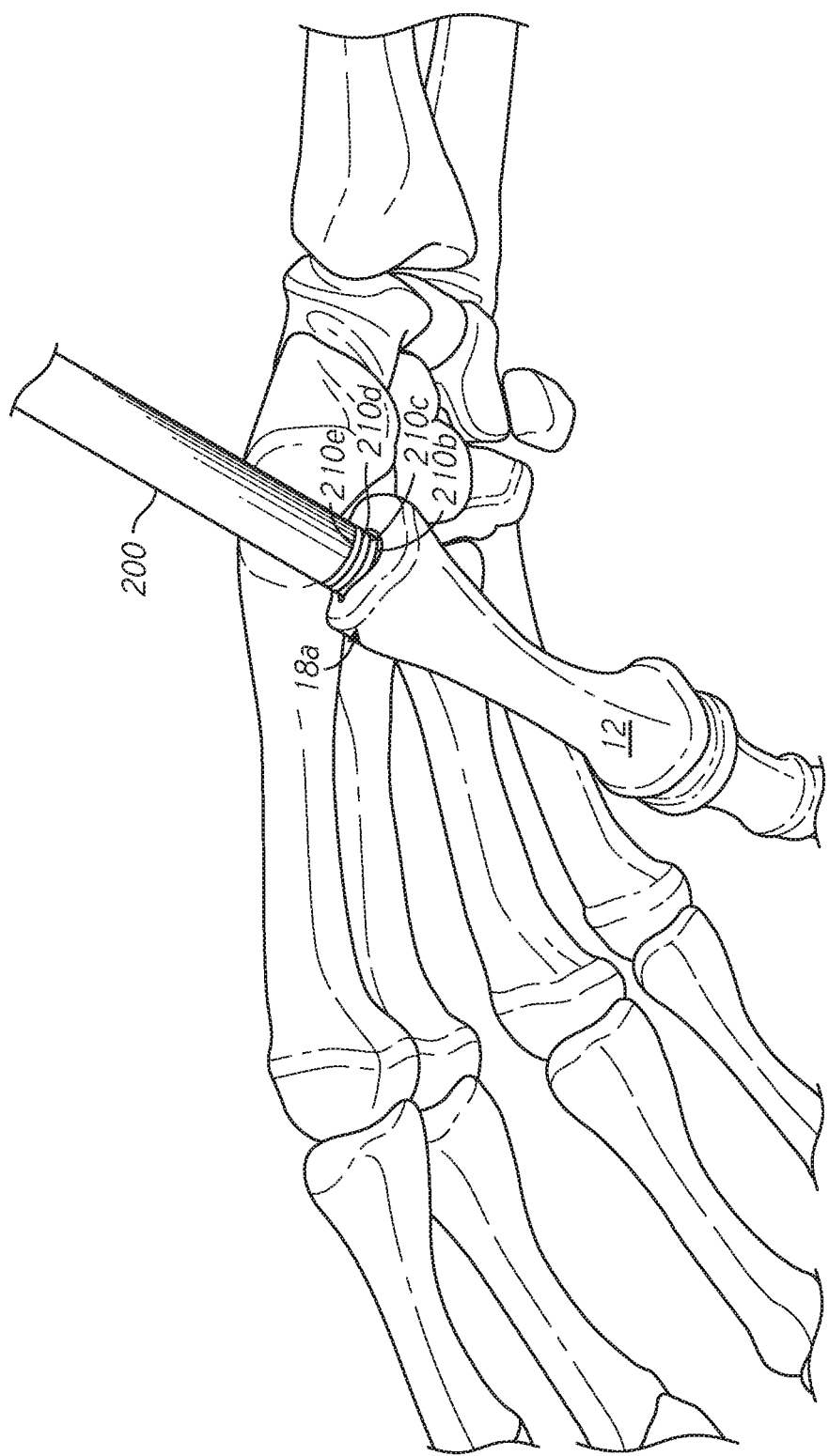
Figure 6L:
Figure 6M:
Figure 6N:
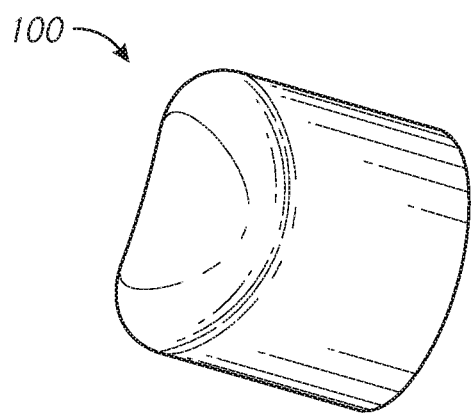
Figure 60:
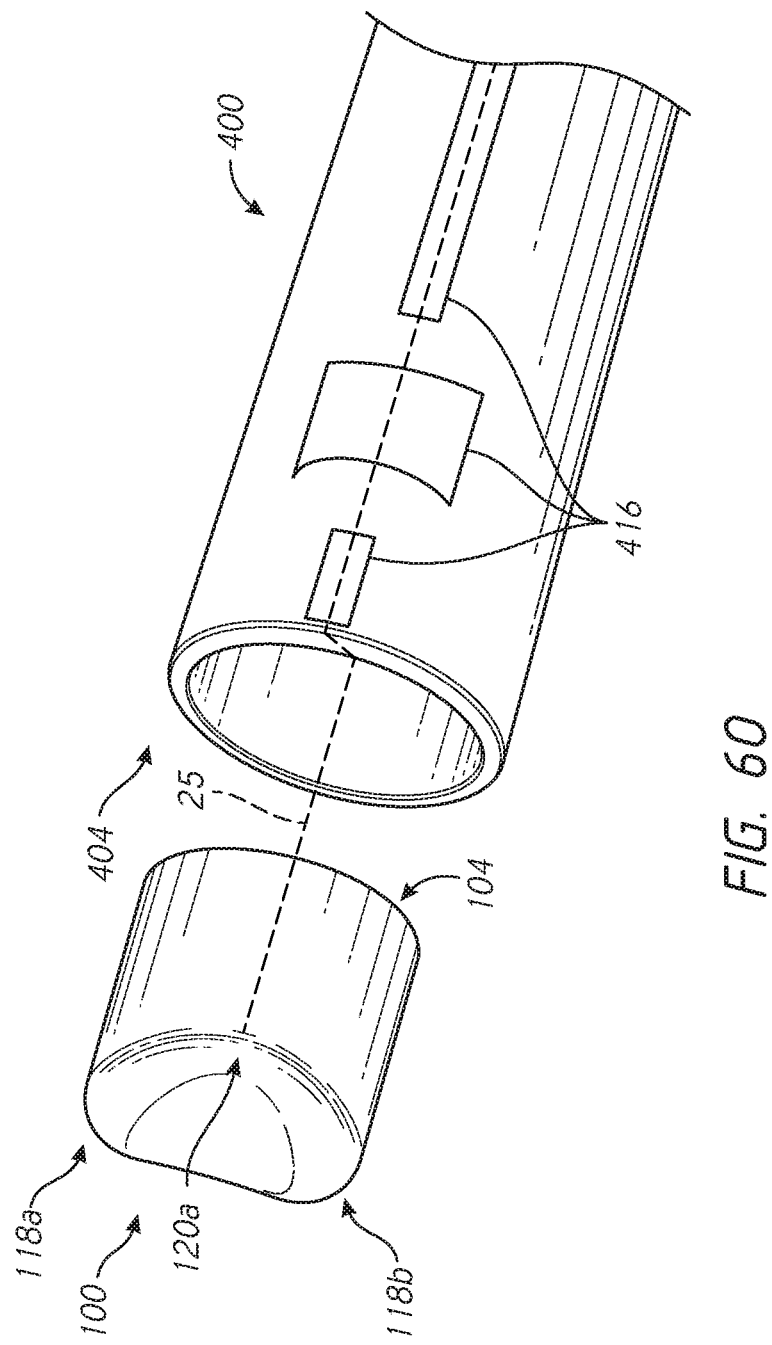
Figure 6P:
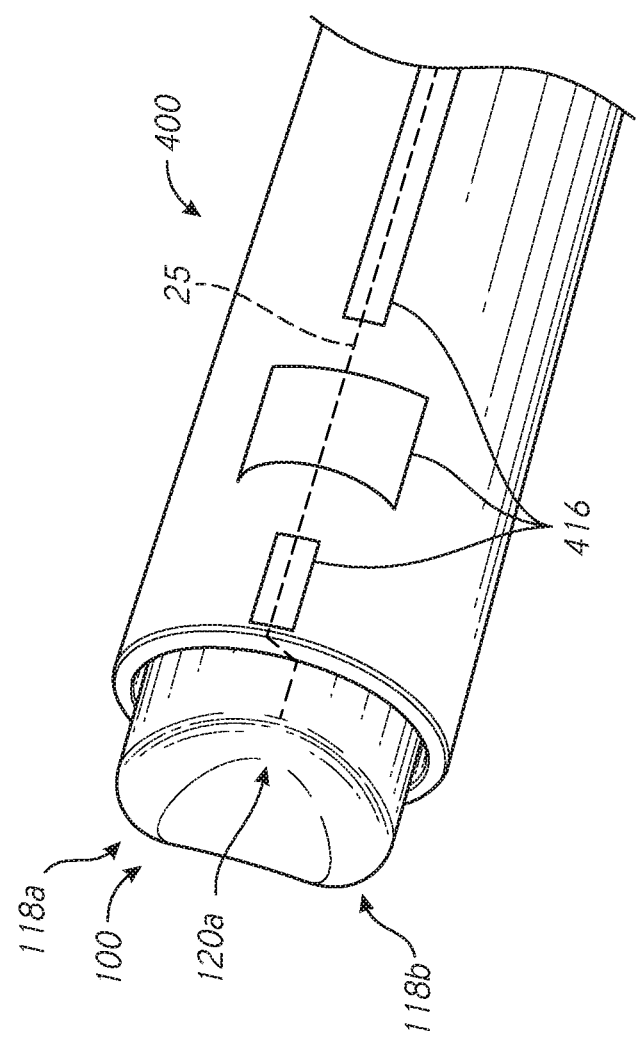
Figure 6Q:
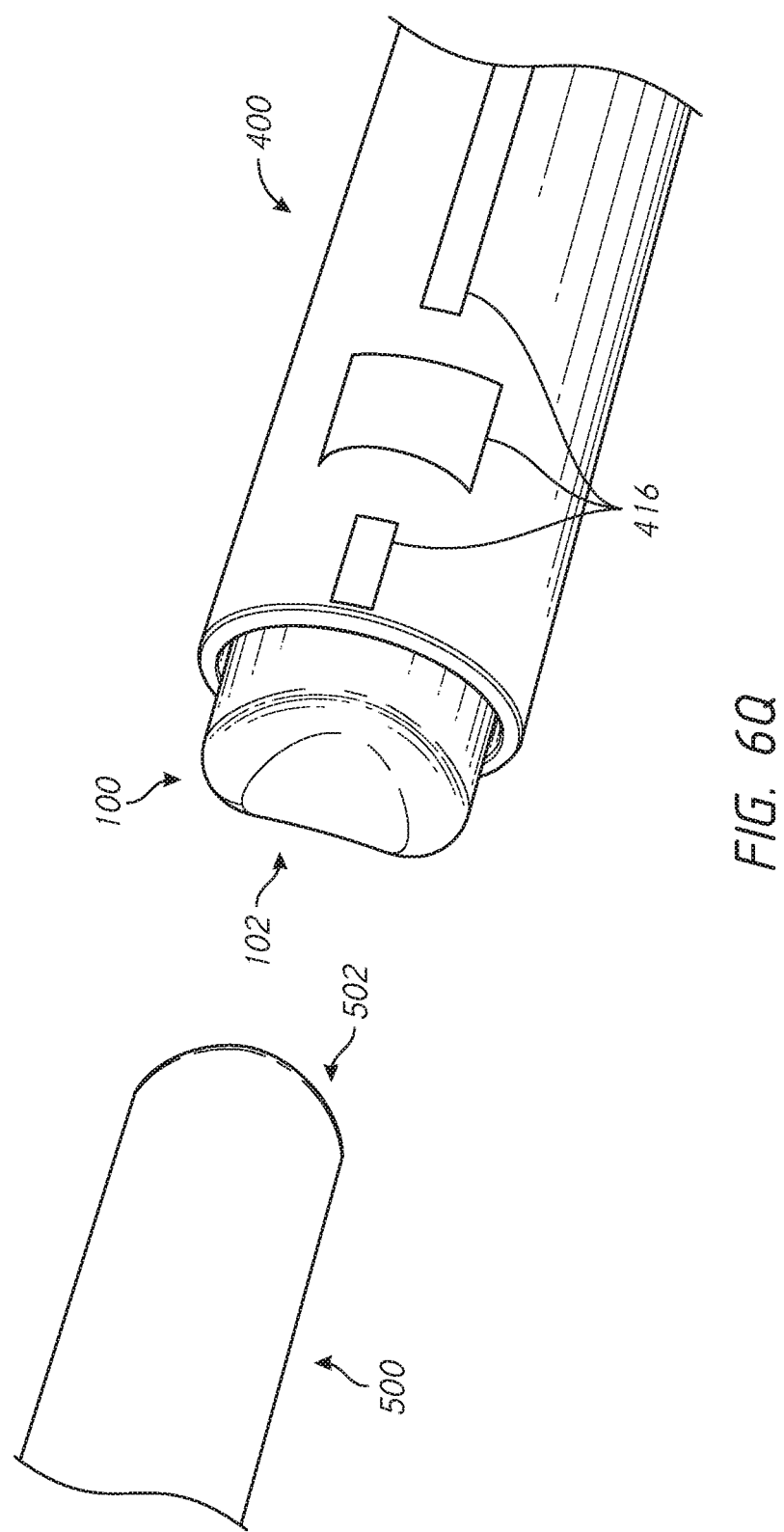
Figure 6R:
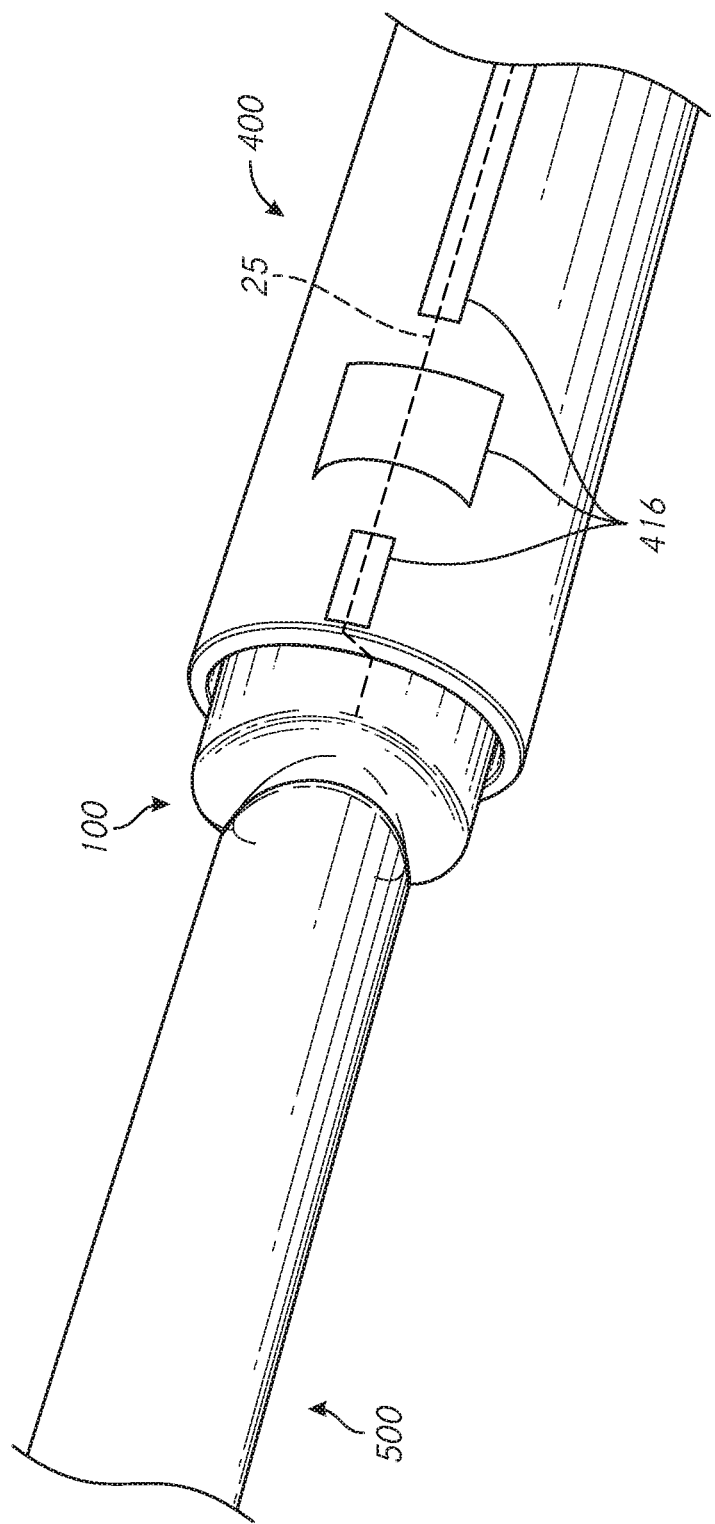
Figure 6S:
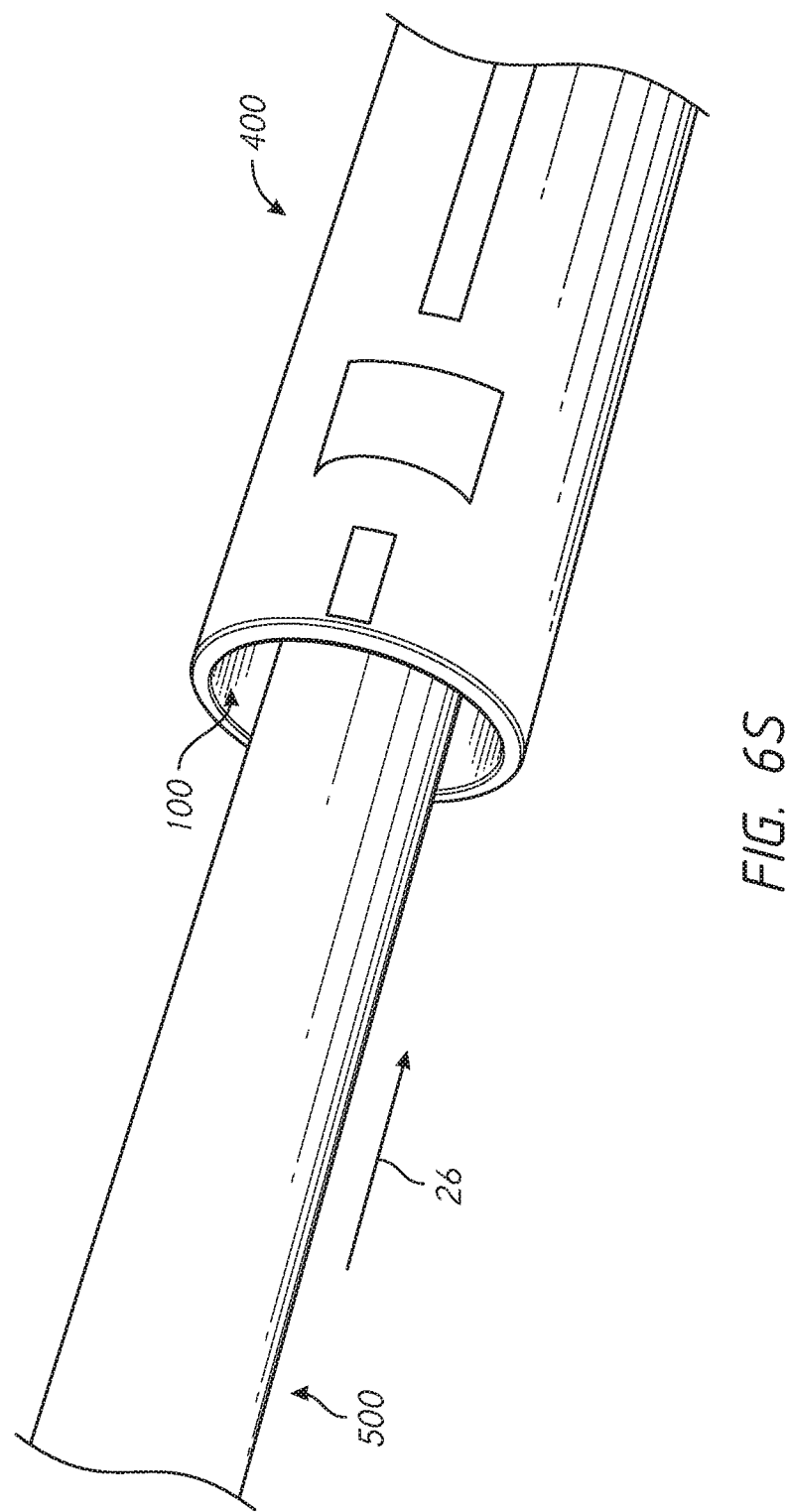
Figure 6T:
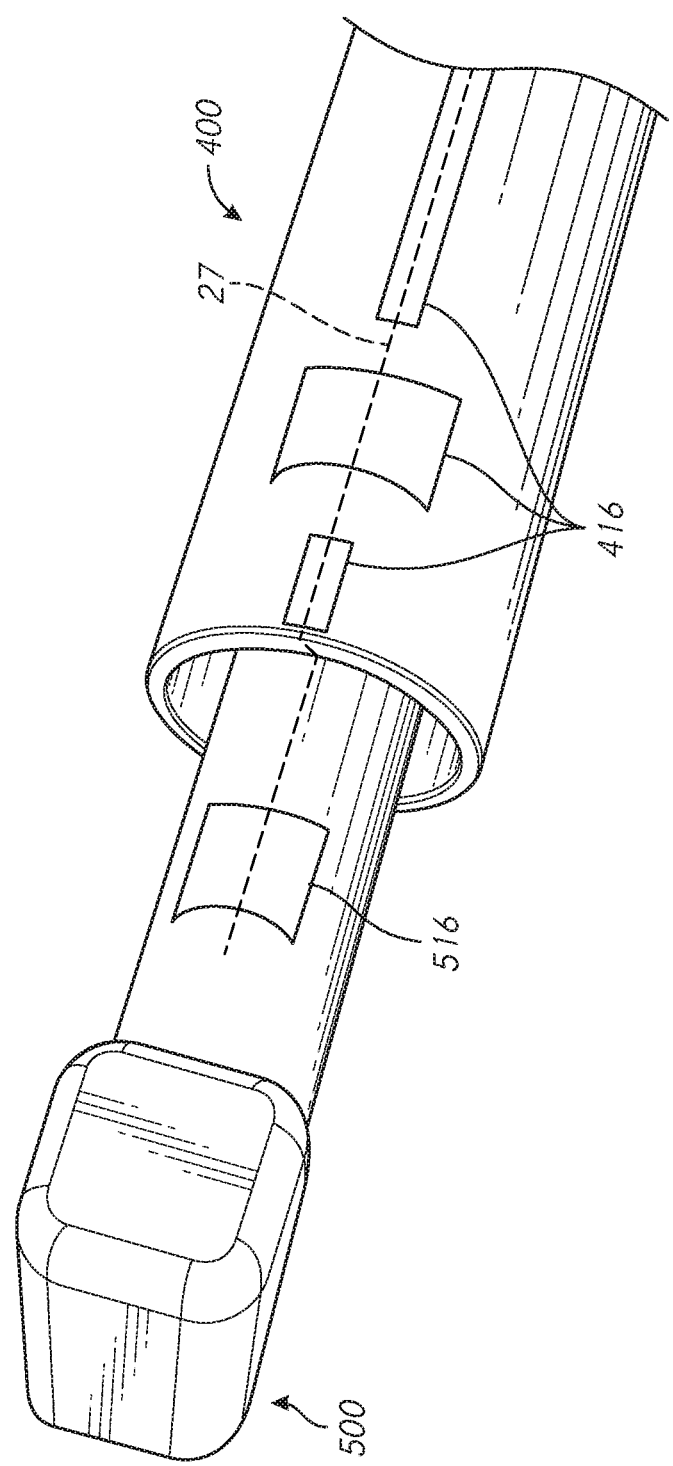
Figure 6V:
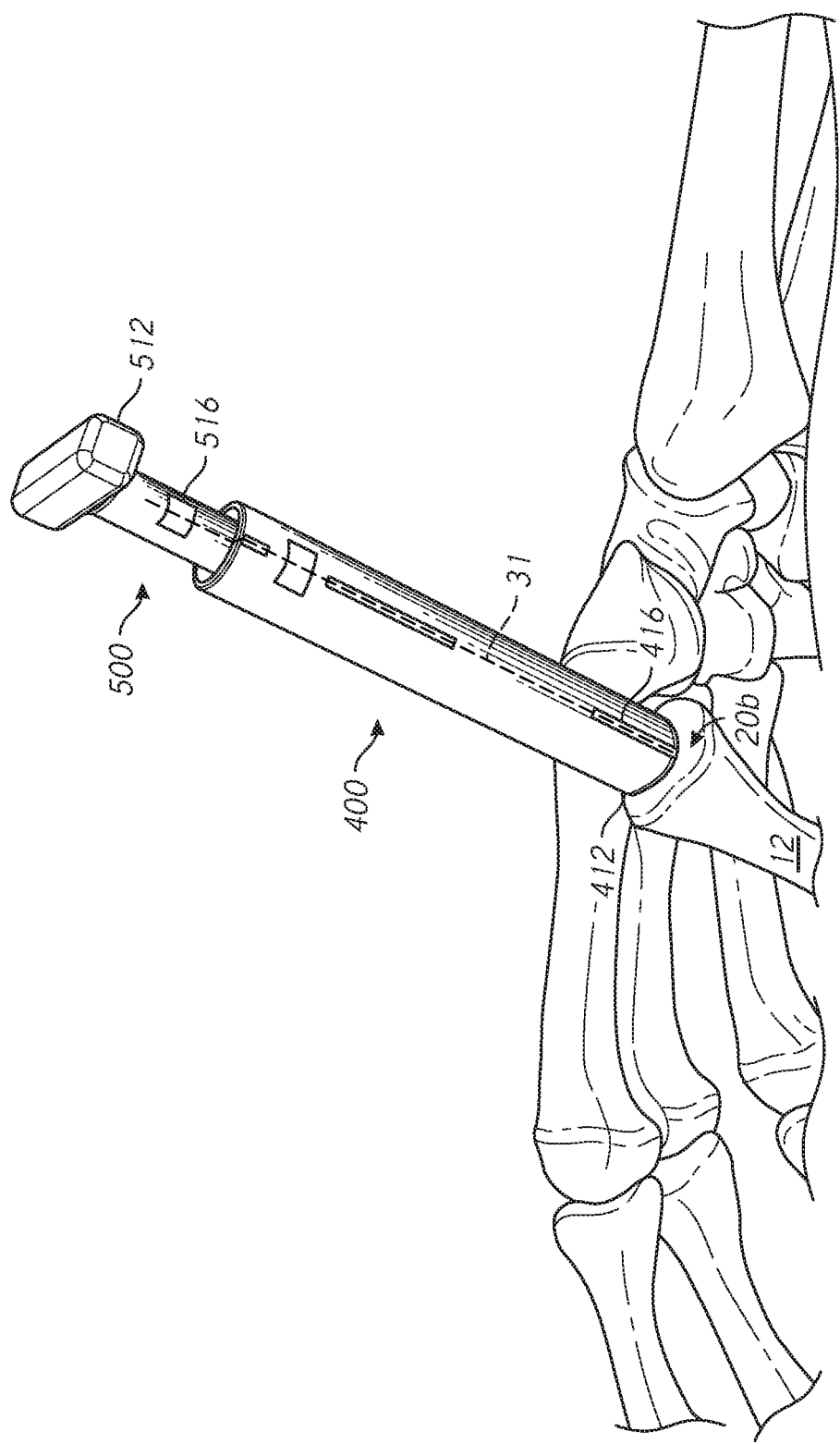
Figure 6X:
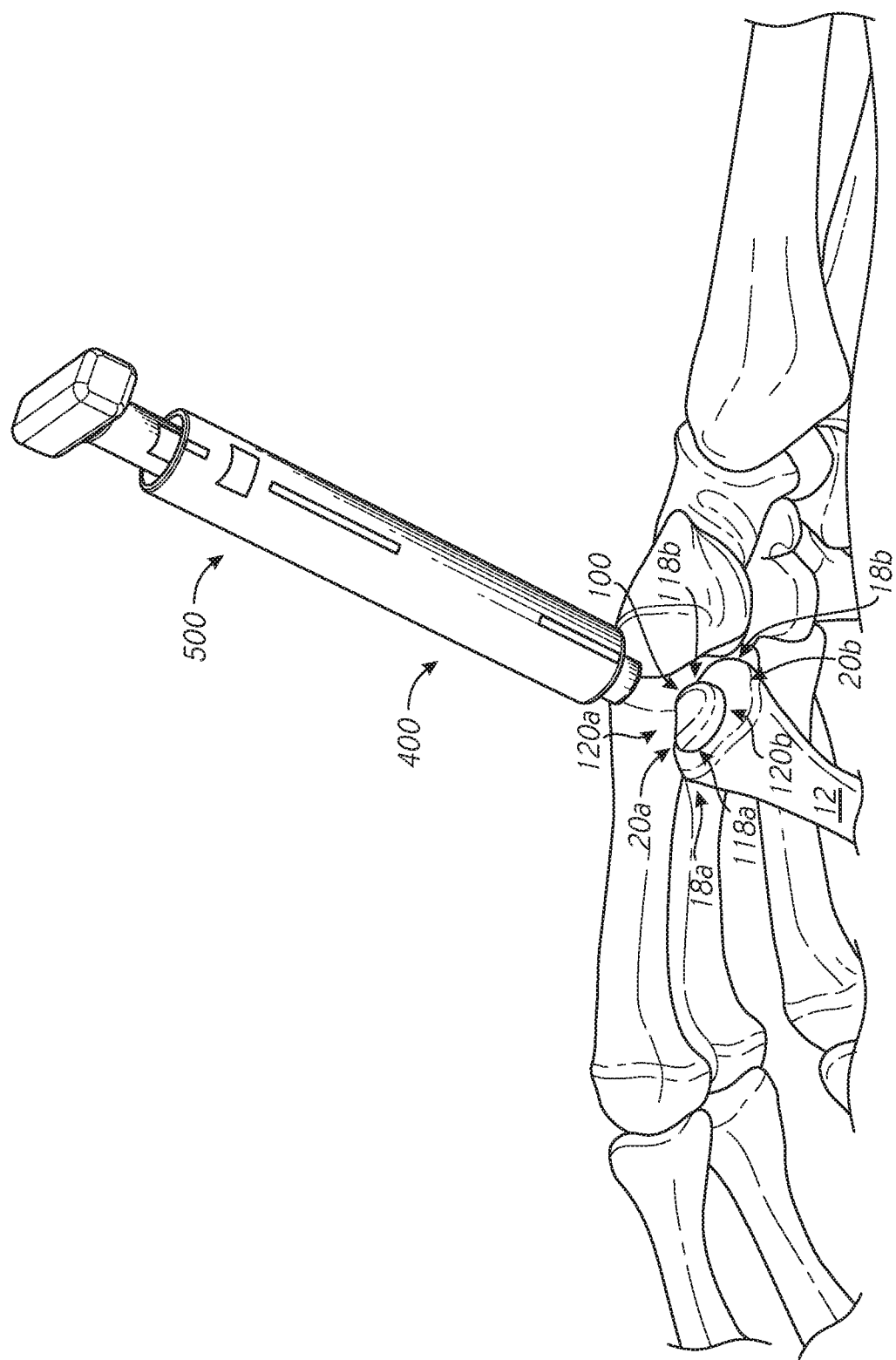
Figure 6Y:
Figure 6Z:
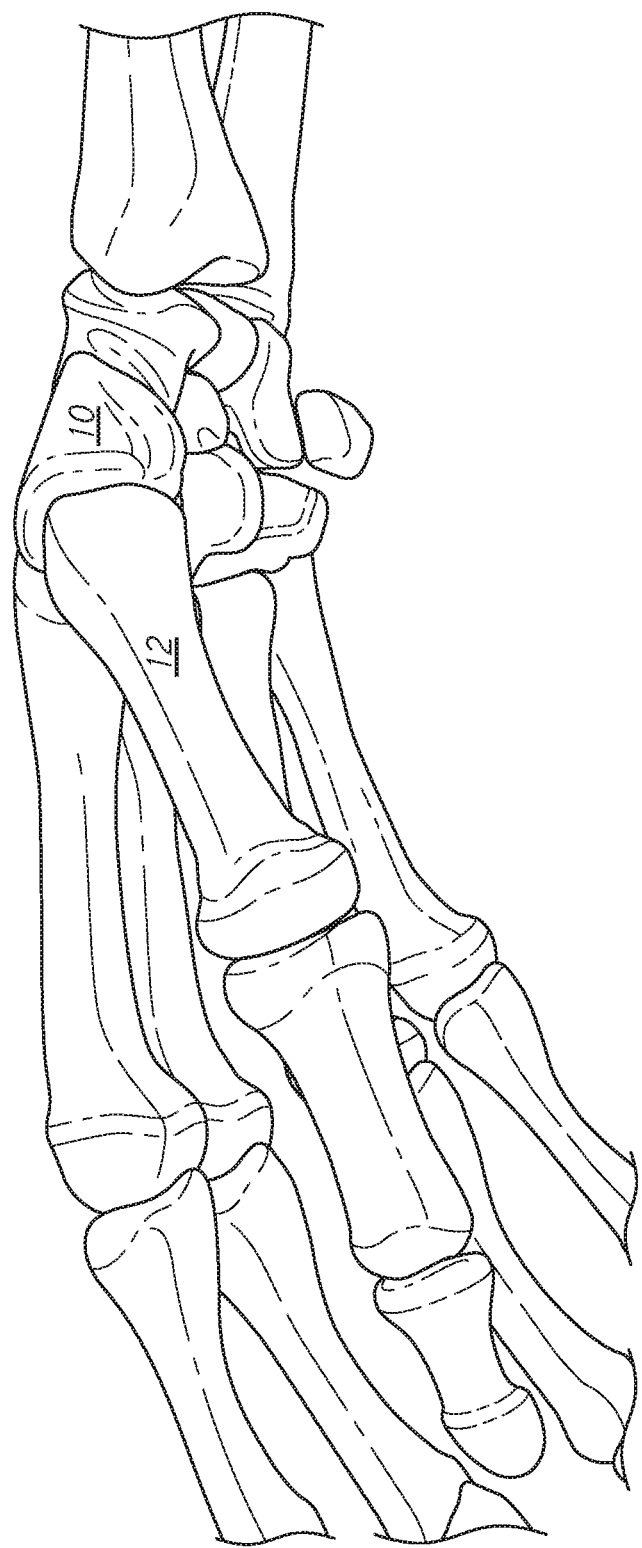

FIGS. 6A-6Z schematically illustrate an example method of positioning an example carpometacarpal implant 100. Although illustrated with reference to the implant 100, the placer 200, the drill bit 300, the introducer 400, and the plunger 500, as described above in detail, other implants, tools, systems, and methods are possible. Although illustrated as positioning the implant 100 in a right hand, positioning in the left hand is also possible.

In FIG. 6A, an incision 14 is made proximate to (e.g., close enough to sufficiently access) the joint between the trapezium 10 and the first metacarpal bone 12. The cartilage between the trapezium 10 and the first metacarpal bone 12 has been worn out or damaged. Additional steps and/or other actions associated with a procedure, such, as, for example, sterilization, anesthesia, site preparation, and the like, may be used; however, details have been omitted from the description of the procedure herein for brevity.

As shown in FIG. 6B, the thumb including the first metacarpal bone 12 can be bent (e.g., downwardly) to expose the joint between the trapezium 10 and the first metacarpal bone 12, including an end surface 16 of the first metacarpal bone 12. Skin, muscle, ligaments, etc. are omitted from FIGS. 6B-6M and 6U-6Z for clarity. The end surface 16 has a generally concave saddle shape including peaks 18a, 18b and troughs 20a, 20b. Surfaces of the implant 100, the placer 200, the introducer 400, and/or the plunger 500 may be contoured to correspond to a surface of one or more others of the implant 100, the placer 200, the introducer 400, and/or the plunger 500, a surface of a metacarpal bone, and/or a surface of a trapezium.

In FIGS. 6C and 6D, a placer 200 is advanced toward the end surface 16 through the incision 14 (FIG. 6A). The placer 200 may be generally longitudinally aligned with the first metacarpal bone 12. In FIG. 6D, the first end 202 of the placer 200 abuts the end surface 16.

In some embodiments, a guide pin 22 is advanced through the lumen 208 of the placer 200 and positioned in or "tamped" at least partially in the first metacarpal bone 16. FIG. 6E shows the guide pin 22 placed using the placer 200. Placement of the guide pin 22 without a placer is also possible. The guide pin 22 may be substantially parallel or parallel with a longitudinal axis of the first metacarpal bone 16, at an angle (e.g., about 90°, less than about 90°, greater than about 90°) to the end surface 16 or a portion (e.g., a certain contour) thereof. The guide pin 22 may be advanced through the anatomy using a trocar or similar device.

FIGS. 6F-6I illustrate the drill bit 300 forming a cavity or recess or hole or aperture or crater or pit or pocket 24 in the first metacarpal bone 12. FIG. 6F shows the drill bit 300 being tracked over the guide pin 22 towards the end surface 16 of the first metacarpal bone 12. The guide pin 22 can help ensure that the drill bit 300 is properly positioned relative to the treatment site (e.g., joint). Forming the cavity 24 without a guide pin 22 is also possible. FIG. 6G shows the inception of formation of the cavity 24 due to rotation about the longitudinal axis of the drill bit 300 and distal longitudinal advancement towards the end surface 16. In the embodiment of FIG. 6H, the flange 312 abuts the end surface 16, which inhibits or prevents further drilling by the drill bit 300. FIG. 6I shows the drill bit 300 being proximally retracted over the guide pin 22 after forming the cavity 24. The cavity 24 has a diameter and depth based on the configuration of the drill bit 300 (e.g., dimensions of the cutters 310a, 310b, 310c, the flange 312, etc.).

In some embodiments, the lateral dimension (e.g., diameter) of the cavity 24 is smaller than the lateral dimension (e.g., diameter) of the implant 100, which may flex radially inwardly. Although illustrated as a cylindrical hole 24, other shapes are also possible (e.g., trapezoidal tapering inwards towards the upper surface). In some embodiments, a lateral dimension and/or cross-sectional area of the cavity 24 is about 5% to about 15% (e.g., about 5%, about 6%, about 7%, about 8%, about 9%, about 10%, about 11%, about 12%, about 13%, about 14%, about 15%, ranges between such values, etc.) narrower or otherwise smaller than the lateral dimension and/or cross-sectional area of the implant 100. The cavity 24 may be coated or otherwise treated prior to positioning of the implant 100.

FIGS. 6F-6I illustrate the placer 200 being used to measure and/or check depth of the cavity 24. In FIG. 6J, the placer 200 has been flipped so the second end 204 faces the cavity 24. In some embodiments, a separate tool is used. The placer 200 is tracked over the guide pin 22 towards and, as shown in FIG. 6K, partially into the cavity 24. Measurement of the cavity 24 without a guide pin 22 is also possible. The bands 210a, 210b, 210c, 210d, 210e are used to measure the depth of the cavity 24. In some embodiments, the depth is measured at the peak 18a. Like using a ruler, a user can visualize the last band that is visible over the peak 18a (e.g., the band 210c in FIG. 6K, corresponding to a depth of about 8 mm). In some embodiments, the depth is measured at the peak 18b, trough 20a, trough 20b, or some other portion of the end surface 16. If the cavity 24 has an incorrect depth, if the second end 204 is not able to fit in the cavity 24, or the second end 204 evidences other issues, the drill bit 300 or another drill bit can be used to correct the defect in the cavity 24. FIG. 6L shows the placer 200 being proximally retracted over the guide pin 22 after measuring the cavity 24.

FIG. 6M shows the guide pin 22 being removed from the first metacarpal bone 12. A sharp distal end of the guide pin 22, which can pierce the bone during tamping and/or help to wedge the guide pin 22 through the bone, is visible. In some embodiments in which an implant comprises a bone anchor, the bone anchor may fit in a hole created by the guide pin.

FIGS. 6N-6T show preparation of the implant 100 for deployment using a deployment system comprising the introducer 400 and the plunger 500. The deployment preparation can be before, during, or after other steps of the procedure. For example, a first user can prepare the implant 100 for deployment while a second user forms the cavity 24, which can reduce overall operation time. In some embodiments, the implant 100 is soaked in saline, water, or another fluid or otherwise treated prior to implantation. In FIG. 6O, the bottom surface 104 of the implant 100 is aligned for placement in the proximal end 404 of the introducer 400. The implant 100 is oriented so that the trough 120a (alternatively, the trough 120b) is rotationally aligned with the indicia 416, as shown by the dashed line 25, which shifts account for the introducer thickness in the perspective view. In the orientation of FIG. 6O, the peaks 118a, 118b should face the top and bottom and the troughs 120a, 120b should face the sides. In FIG. 6P, the implant is positioned partially in the introducer 400. Further advancement into the introducer 400 may be limited by the flared shape 414.

FIG. 6Q shows the use of the distal end 502 of the plunger 500 approaching the upper surface 102 of the implant 100. The topography or contours of the distal end 502 of the plunger 500 may correspond to the topography or contours of the end surface 102 of the implant. FIG. 6R shows engagement of the plunger 500 with the implant 100. The indicia 416 of the introducer 400 show that the implant 100 is still properly aligned in the introducer 400. In FIG. 6S, the plunger 500 is advanced in the direction shown by the arrow 26 to advance the implant 100 into the introducer 400. In some embodiments, the plunger 500 is held stationary and the introducer 400 is advanced in the direction opposite the arrow 26. In some embodiments, the plunger 500 is advanced in the direction 26 and the introducer 400 is advanced in the direction opposite the arrow 26. The plunger 500 can help advance the implant 100 past the flared shape 414, radially inwardly compressing the implant 100. In some embodiments, the implant 100 is compressed by between about 5% and about 50% (e.g., about 5%, about 10%, about 15%, about 20%, about 25%, about 30%, about 35%, about 40%, about 45%, about 50%, ranges between these values, etc.) by the flared shape 414 of the introducer 400. In FIG. 6T, the plunger 500 is advanced to a deployment position. The indicia 516 and the indicia 416 can be used to verify that the implant 100, now proximate to the distal end 402 of the introducer 400, is still aligned, as shown by the dashed line 27, which shifts account for the introducer thickness in the perspective view. If the implant 100 is not aligned, the implant 100 may be deployed from the distal end 402 of the introducer by further advancing the plunger 500, and the loading process may be started over at FIG. 6N using the same implant 100 or a different implant. In some embodiments in which a same implant 100 is used, the implant may be treated prior to reloading (e.g., soaked for a period of time prior to reloading).

FIGS. 6U-6X show deployment of the implant 100 in the cavity 24 in the first metacarpal bone 12. In FIG. 6U, the introducer 400 is advanced towards the cavity 24. During the advancement, the indicia 416 are aligned with contours of the end surface 16, as shown by the dashed line 29, which shifts account for the introducer thickness in the perspective view. In some embodiments, the line of the indicia 416 is aligned to a trough 20b of the end surface 16. Various alignment processes described herein may be described as concave-to-convex.

In FIG. 6V, the neck portion 410 of the introducer 400 is positioned at least partially within the cavity 24 in which the implant 100 will be positioned. The shoulder 412 acts as a depth stop. FIG. 6V also shows the alignment of the indicia 416 with the trough 20b and the indicia 516, as shown by the dashed line 31, which shifts account for the introducer thickness in the perspective view. In some embodiments, the introducer 400 is sized, shaped, and otherwise configured to that the neck portion 410 fits generally snugly in the cavity 24. The plunger 500 is illustrated with the head portion 512 in a first position.

In FIG. 6W, the head portion 512 is distally advanced in the direction of the arrow 28 to urge the implant 100 out of the distal end 402 of the introducer 400 and in the cavity 24. The plunger 500 can be operated manually and/or with the assistance of an external power-assist device (e.g., mechanically, pneumatically, hydraulically, etc.), as desired or required. The lower surface 104 of the implant 100 is located at or proximate to the bottom or floor of the cavity 24.

FIG. 6X shows the implant 100 after being deployed in the anatomical position and the deployment device being proximally retracted. The peak 118a of the implant 100 is aligned with the peak 18a of the end surface 16, the peak 118b of the implant 100 is aligned with the trough 18b of the end surface 16, the trough 120a of the implant 100 is aligned with the trough 20a of the end surface 16, and the trough 120b of the implant 100 is aligned with the trough 20b of the end surface 16. If the alignment is incorrect, the guide pin 22, for example, can be used to urge the implant 100 out of the cavity 24. The implant is between about 1 mm and about 3 mm proud above the end surface 16, for example measured peak-to-peak (e.g., 18a to 118a or 18b to 118b) or trough-to-trough (e.g., 20a to 120a or 20b to 120b).

In FIGS. 6Y and 6Z, the thumb is bent so that the first metacarpal bone 12 is in a normal anatomical position with respect to the trapezium 10. The incision 14 may then be stitched or otherwise closed.

Although several embodiments and examples are disclosed herein, the present application extends beyond the specifically disclosed embodiments to other alternative embodiments and/or uses of the various inventions and modifications, and/or equivalents thereof. It is also contemplated that various combinations or subcombinations of the specific features and aspects of the embodiments may be made and still fall within the scope of the inventions. Accordingly, various features and aspects of the disclosed embodiments can be combined with or substituted for one another in order to form varying modes of the disclosed inventions. Thus, the scope of the various inventions disclosed herein should not be limited by any particular embodiments described above. While the embodiments disclosed herein are susceptible to various modifications, and alternative forms, specific examples thereof have been shown in the drawings and are described in detail herein. However, the inventions of the present application are not limited to the particular forms or methods disclosed, but, to the contrary, cover all modifications, equivalents, and alternatives falling within the spirit and scope of the various embodiments described and the appended claims. Further, the disclosure herein of any particular feature, aspect, method, property, characteristic, quality, attribute, element and/or the like in connection with an implementation or embodiment can be used in all other implementations or embodiments set forth herein.

In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, any structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages.

The methods disclosed herein include certain actions taken by a practitioner; however, they can also include any third-party instruction of those actions, either expressly or by implication. For example, actions such as "deploying an implant" include "instructing deployment of an implant." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 mm" includes "1 mm." Phrases preceded by a term such as "substantially" include the recited phrase and should be interpreted based on the circumstances (e.g., as much as reasonably possible under the circumstances). For example, "substantially rigid" includes "rigid," and "substantially parallel" includes "parallel."

What is claimed is:

1. A method of positioning an implant having a contoured upper surface in a carpometacarpal joint, wherein the carpometacarpal joint comprises a carpometacarpal bone and a surface of a trapezium, the method comprising:
   (a) loading an implant in an implant deployment system, wherein the implant deployment system comprises:
      an introducer comprising a tube extending from a distal end to a proximal end and a lumen defined therein, wherein the lumen has a flared shape starting from the proximal end, wherein at least a portion of the lumen has a progressively reducing inside diameter in the proximal to distal direction, and the distal end of the tube forming a neck, whereby the neck has a smaller diameter than the proximal end of the lumen, the introducer further comprising a first alignment indicia; and
      a plunger comprising a second alignment indicia,
      wherein loading the implant comprises aligning the contoured upper surface of the implant with the first alignment indicia and inserting the implant into the lumen from the proximal end;
   (b) aligning the implant deployment system with a recess that has been prepared in the carpometacarpal bone, the recess facing the surface of the trapezium;
   (c) inserting the neck of the introducer at least partially into the recess; and
   (d) deploying the implant out of the implant deployment system and at least partially into the recess,
   wherein, after deployment, the implant is 1 mm to 3 mm proud.

2. The method of claim 1, wherein aligning the implant deployment system with the recess in the carpometacarpal bone comprises aligning the first alignment indicia with a surface feature of the carpometacarpal bone.

3. The method of claim 1, further comprising the following step after the step (a) but before the step (d): radially compressing the implant in the implant deployment system by distally urging the implant through the lumen of the introducer using the plunger, whereby the flared shape of the lumen radially compresses the implant.

4. The method of claim 1, further comprising the following steps before step (a) or step (b):
   tamping a guide pin in the carpometacarpal bone through a lumen of a placer, the placer comprising a first contoured end and a second end comprising measurement bands;
   forming the recess in the carpometacarpal bone, wherein forming the recess comprises tracking a drill bit over the guide pin; and
   measuring a depth of the recess in the carpometacarpal bone using the measurement bands, wherein measuring the depth comprises tracking the placer over the guide pin.

5. The method of claim 1, wherein aligning the contoured upper surface of the implant with the first alignment indicia comprises aligning the first alignment indicia with a surface feature of the contoured upper surface of the implant.

6. The method of claim 1, wherein loading the implant in the implant deployment system further comprises aligning a contoured end of the plunger with the contoured upper surface of the implant.

7. The method of claim 6, wherein loading the implant in the implant deployment system further comprises:
   inserting the plunger at least partially into the lumen of the introducer; and
   verifying that the first alignment indicia is aligned with the second alignment indicia.

8. The method of claim 1, wherein the first alignment indicia comprise at least first and second markings on the exterior of the tube, wherein the first marking is proximate the proximate end of the tube and the second marking is proximate the distal end of the tube, wherein the first and second markings are axially aligned along a longitudinal axis of the tube, and wherein:
   loading the implant in the implant deployment system comprises aligning the contoured upper surface of the implant with the first marking; and aligning the implant deployment system with the recess includes aligning the second marking with a feature of the carpometacarpal bone.

9. A method of positioning an implant having a contoured upper surface in a carpometacarpal joint, wherein the carpometacarpal joint comprises a carpometacarpal bone and a surface of a trapezium, the method comprising:
(a) tamping a guide pin in the carpometacarpal bone through a lumen of a placer, the placer comprising a first contoured end and a second end comprising measurement bands;
(b) forming a recess in the carpometacarpal bone, wherein forming the recess comprises tracking a drill bit over the guide pin; and
(c) measuring a depth of the recess in the carpometacarpal bone using the measurement bands, wherein measuring the depth comprises tracking the placer over the guide pin;
(d) loading the implant in an implant deployment system, the implant deployment system comprising:
an introducer comprising a first alignment indicia and a lumen defined therein, wherein the lumen has a flared shape starting from a proximal end, wherein at least a portion of the lumen has a progressively reducing inside diameter in the proximal to distal direction; and
a plunger comprising a second alignment indicia,
wherein loading the implant comprises aligning the contoured upper surface of the implant with the first alignment indicia;
(e) aligning the implant deployment system with the recess in the carpometacarpal bone,
(f) deploying the implant out of the implant deployment system and at least partially into the recess.

10. The method of claim 9, wherein aligning the implant deployment system comprises aligning the first alignment indicia with a surface feature of the carpometacarpal bone.

11. The method of claim 9, wherein, after deploying the implant, the implant is 1 mm to 3 mm proud.

12. The method of claim 9, further comprising the following step after the step (d) but before the step (f): radially compressing the implant in the implant deployment system by distally urging the implant through the lumen of the introducer using the plunger, whereby the flared shape of the lumen radially compresses the implant.

13. The method of claim 9, further comprising:
removing the guide pin before the step (e).

14. The method of claim 9, wherein loading the implant in the implant deployment system further comprises:
inserting the implant into a lumen of the introducer; and
aligning a contoured end of the plunger with the contoured upper surface of the implant.

15. The method of claim 14, wherein loading the implant in the implant deployment system further comprises:
inserting the plunger at least partially into the lumen of the introducer; and
verifying that the first alignment indicia is aligned with the second alignment indicia.

16. The method of claim 9, wherein aligning the contoured upper surface of the implant with the first alignment indicia comprises aligning the first alignment indicia with a surface feature of the contoured upper surface of the implant.

17. The method of claim 9, wherein the introducer comprises a tube extending from a distal end to a proximal end and the first alignment indicia comprise at least first and second markings on the exterior of the tube, wherein the first marking is proximate the proximal end of the tube and the second marking is proximate the distal end of the tube, wherein the first and second markings are axially aligned along a longitudinal axis of the tube, and wherein:
loading the implant in the implant deployment system comprises aligning the contoured upper surface of the implant with the first marking; and
aligning the implant deployment system with the recess includes aligning the second marking with a feature of the carpometacarpal bone.

18. A method of positioning an implant having a contoured upper surface in a carpometacarpal joint, wherein the carpometacarpal joint comprises a carpometacarpal bone and a surface of a trapezium, the method comprising:
(a) loading an implant in an implant deployment system, wherein the implant deployment system comprises:
an introducer comprising a tube extending from a distal end to a proximal end and a lumen defined therein, wherein the lumen has a flared shape starting from the proximal end, wherein at least a portion of the lumen has a progressively reducing inside diameter in the proximal to distal direction, the introducer further comprising a first alignment indicia; and
a plunger comprising a second alignment indicia;
wherein loading the implant comprises aligning the contoured upper surface of the implant with the first alignment indicia and inserting the implant into the lumen from the proximal end;
(b) aligning the implant deployment system with a recess that has been prepared in the carpometacarpal bone, the recess facing the surface of the trapezium;
(c) distally urging the implant through the lumen of the introducer using the plunger, whereby the flared shape of the lumen radially compresses the implant;
(d) deploying the implant out of the implant deployment system and at least partially into the recess;
wherein, after deployment, the implant is 1 mm to 3 mm proud.

19. The method of claim 18, wherein aligning the contoured upper surface of the implant with the first alignment indicia comprises aligning the first alignment indicia with a surface feature of the contoured upper surface of the implant.

20. The method of claim 18, wherein loading the implant in the implant deployment system further comprises aligning a contoured end of the plunger with the contoured upper surface of the implant.

21. The method of claim 20, wherein loading the implant in the implant deployment system further comprises:
inserting the plunger at least partially into the lumen of the introducer; and
verifying that the first alignment indicia is aligned with the second alignment indicia.

22. The method of claim 18, further comprising the following steps before step (a) or step (b):
tamping a guide pin in the carpometacarpal bone through a lumen of a placer, the placer comprising a first contoured end and a second end comprising measurement bands;
forming the recess in the carpometacarpal bone, wherein forming the recess comprises tracking a drill bit over the guide pin; and
measuring a depth of the recess in the carpometacarpal bone using the measurement bands, wherein measuring the depth comprises tracking the placer over the guide pin.

23. The method of claim 18, wherein the first alignment indicia comprise at least first and second markings on the exterior of the tube, wherein the first marking is proximate the distal end of the tube and the second marking is proximate the proximal end of the tube, wherein the first and second markings are axially aligned along a longitudinal axis of the tube, and wherein:
- loading the implant in the implant deployment system comprises aligning the contoured upper surface of the implant with the first marking; and
- aligning the implant deployment system with the recess includes aligning the second marking with a feature of the carpometacarpal bone.

* * * * *